US012653539B2

(12) United States Patent
Chen et al.

(10) Patent No.: US 12,653,539 B2
(45) Date of Patent: Jun. 16, 2026

(54) LEFT ATRIAL APPENDAGE CLOSURE DEVICE

(71) Applicant: BOSTON SCIENTIFIC SCIMED, INC., Maple Grove, MN (US)

(72) Inventors: Jan-Hung Chen, St. Paul, MN (US); Harishankar Natesan, Shoreview, MN (US); Thyna M. Chau, Woodbury, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/490,986

(22) Filed: Oct. 20, 2023

(65) Prior Publication Data

US 2024/0041469 A1 Feb. 8, 2024

Related U.S. Application Data

(63) Continuation of application No. 17/857,513, filed on Jul. 5, 2022, now Pat. No. 12,383,278.

(Continued)

(51) Int. Cl.
*A61B 17/12* (2006.01)
(52) U.S. Cl.
CPC .. *A61B 17/12172* (2013.01); *A61B 17/12031* (2013.01); *A61B 17/12122* (2013.01); *A61B 2017/1205* (2013.01)
(58) Field of Classification Search
CPC ........ A61B 17/12172; A61B 17/12031; A61B 17/12122; A61B 2017/1205; A61B 17/12177
See application file for complete search history.

(56) References Cited

U.S. PATENT DOCUMENTS

| | | | |
|---|---|---|---|
| 178,283 | A | 6/1876 | French |
| 1,967,318 | A | 7/1934 | Monahan |

(Continued)

FOREIGN PATENT DOCUMENTS

| | | |
|---|---|---|
| CN | 1399571 A | 2/2003 |
| CN | 202143640 U | 2/2012 |

(Continued)

OTHER PUBLICATIONS

International Search Report and Written Opinion dated Aug. 3, 2004 for International Application No. PCT/US2004/008109.

(Continued)

*Primary Examiner* — Shaun L David
*Assistant Examiner* — Rachael L Geiger
(74) *Attorney, Agent, or Firm* — Seager, Tufte & Wickhem LLP

(57) ABSTRACT

A left atrial appendage closure device may include an expandable framework having a plurality of struts joined at a proximal and distal hub. When the framework is fully constrained in a first position, a first segment of struts extends distally from the distal hub parallel to a central longitudinal axis to a first bend and a second segment of struts extends from the first bend proximally. A first amount of the framework is unconstrained in a second position, where the first segment extends distally from the distal hub parallel to the central longitudinal axis to the first bend, the second segment extends from the first bend proximally and radially outward to a second bend, a third segment of struts extends from the second bend proximally and radially inward to a third bend, and a fourth segment of struts extends from the third bend proximally to within the delivery sheath.

20 Claims, 9 Drawing Sheets

Related U.S. Application Data

(60) Provisional application No. 63/219,696, filed on Jul. 8, 2021.

(56) References Cited

U.S. PATENT DOCUMENTS

| | | | |
|---|---|---|---|
| 3,402,710 A | 9/1968 | Paleschuck |
| 3,540,431 A | 11/1970 | Mobin-Uddin |
| 3,557,794 A | 1/1971 | Van Patten |
| 3,638,652 A | 2/1972 | Kelley |
| 3,811,449 A | 5/1974 | Gravlee et al. |
| 3,844,302 A | 10/1974 | Klein |
| 3,874,388 A | 4/1975 | King et al. |
| 4,007,743 A | 2/1977 | Blake |
| 4,108,420 A | 8/1978 | West et al. |
| 4,175,545 A | 11/1979 | Termanini |
| 4,309,776 A | 1/1982 | Berguer |
| 4,341,218 A | 7/1982 | Ü |
| 4,364,392 A | 12/1982 | Strother et al. |
| 4,425,908 A | 1/1984 | Simon |
| 4,545,367 A | 10/1985 | Tucci |
| 4,585,000 A | 4/1986 | Hershenson |
| 4,603,693 A | 8/1986 | Conta et al. |
| 4,611,594 A | 9/1986 | Grayhack et al. |
| 4,619,246 A | 10/1986 | Molgaard-Nielsen et al. |
| 4,638,803 A | 1/1987 | Rand et al. |
| 4,665,906 A | 5/1987 | Jervis |
| 4,681,588 A | 7/1987 | Ketharanathan et al. |
| 4,710,192 A | 12/1987 | Liotta et al. |
| 4,718,417 A | 1/1988 | Kittrell et al. |
| 4,759,348 A | 7/1988 | Cawood et al. |
| 4,781,177 A | 11/1988 | Lebigot |
| 4,793,348 A | 12/1988 | Palmaz |
| 4,827,907 A | 5/1989 | Tashiro |
| 4,832,055 A | 5/1989 | Palestrant |
| 4,873,978 A | 10/1989 | Ginsburg |
| 4,917,089 A | 4/1990 | Sideris |
| 4,921,484 A | 5/1990 | Hillstead |
| 4,960,412 A | 10/1990 | Fink |
| 4,966,150 A | 10/1990 | Etienne et al. |
| 4,998,972 A | 3/1991 | Chin et al. |
| 5,037,810 A | 8/1991 | Saliba, Jr. |
| 5,041,090 A | 8/1991 | Scheglov et al. |
| 5,041,093 A | 8/1991 | Chu |
| 5,042,707 A | 8/1991 | Taheri |
| 5,053,009 A | 10/1991 | Herzberg |
| 5,064,435 A | 11/1991 | Porter |
| 5,071,407 A | 12/1991 | Termin et al. |
| 5,078,736 A | 1/1992 | Behl |
| 5,098,440 A | 3/1992 | Hillstead |
| 5,108,418 A | 4/1992 | Lefebvre |
| 5,108,420 A | 4/1992 | Marks |
| 5,108,474 A | 4/1992 | Riedy et al. |
| 5,116,360 A | 5/1992 | Pinchuk et al. |
| 5,122,136 A | 6/1992 | Guglielmi et al. |
| 5,171,259 A | 12/1992 | Inoue |
| 5,171,383 A | 12/1992 | Sagaye et al. |
| 5,176,692 A | 1/1993 | Wilk et al. |
| 5,192,301 A | 3/1993 | Kamiya et al. |
| 5,211,658 A | 5/1993 | Clouse |
| 5,234,458 A | 8/1993 | Metais |
| 5,256,146 A | 10/1993 | Ensminger et al. |
| 5,258,000 A | 11/1993 | Gianturco |
| 5,258,042 A | 11/1993 | Mehta |
| 5,279,539 A | 1/1994 | Bohan et al. |
| 5,284,488 A | 2/1994 | Sideris |
| 5,304,184 A | 4/1994 | Hathaway et al. |
| 5,306,234 A | 4/1994 | Johnson |
| 5,312,341 A | 5/1994 | Turi |
| 5,329,942 A | 7/1994 | Gunther et al. |
| 5,334,217 A | 8/1994 | Das |
| 5,344,439 A | 9/1994 | Otten |
| 5,350,398 A | 9/1994 | Pavcnik et al. |
| 5,350,399 A | 9/1994 | Erlebacher et al. |
| 5,353,784 A | 10/1994 | Nady-Mohamed |
| 5,366,460 A | 11/1994 | Eberbach |
| 5,366,504 A | 11/1994 | Andersen et al. |
| 5,370,657 A | 12/1994 | Irie |
| 5,375,612 A | 12/1994 | Cottenceau et al. |
| 5,397,331 A | 3/1995 | Himpens et al. |
| 5,397,355 A | 3/1995 | Marin et al. |
| 5,409,444 A | 4/1995 | Kensey et al. |
| 5,417,699 A | 5/1995 | Klein et al. |
| 5,421,832 A | 6/1995 | Lefebvre |
| 5,425,744 A | 6/1995 | Fagan et al. |
| 5,427,119 A | 6/1995 | Swartz et al. |
| 5,433,727 A | 7/1995 | Sideris |
| 5,443,454 A | 8/1995 | Tanabe et al. |
| 5,443,478 A | 8/1995 | Purdy et al. |
| 5,451,235 A | 9/1995 | Lock et al. |
| 5,454,365 A | 10/1995 | Bonutti |
| 5,464,408 A | 11/1995 | Duc |
| 5,469,867 A | 11/1995 | Schmitt |
| 5,490,856 A | 2/1996 | Person et al. |
| 5,497,774 A | 3/1996 | Swartz et al. |
| 5,499,975 A | 3/1996 | Cope et al. |
| 5,499,995 A | 3/1996 | Teirstein |
| 5,522,790 A | 6/1996 | Moll et al. |
| 5,522,822 A | 6/1996 | Phelps et al. |
| 5,522,836 A | 6/1996 | Palermo |
| 5,527,322 A | 6/1996 | Klein et al. |
| 5,527,338 A | 6/1996 | Purdy |
| 5,558,093 A | 9/1996 | Pomeranz et al. |
| 5,558,652 A | 9/1996 | Henke |
| 5,569,204 A | 10/1996 | Cramer et al. |
| 5,591,196 A | 1/1997 | Marin et al. |
| 5,614,204 A | 3/1997 | Cochrum |
| 5,634,936 A | 6/1997 | Linden et al. |
| 5,634,942 A | 6/1997 | Chevillon et al. |
| 5,637,097 A | 6/1997 | Yoon |
| 5,643,282 A | 7/1997 | Kieturakis |
| 5,643,292 A | 7/1997 | Hart |
| 5,649,953 A | 7/1997 | Lefebvre |
| 5,653,690 A | 8/1997 | Booth et al. |
| 5,662,671 A | 9/1997 | Barbut et al. |
| 5,669,933 A | 9/1997 | Simon et al. |
| 5,681,345 A | 10/1997 | Euteneuer |
| 5,681,347 A | 10/1997 | Cathcart et al. |
| 5,683,411 A | 11/1997 | Kavteladze et al. |
| 5,690,671 A | 11/1997 | McGurk et al. |
| 5,693,067 A | 12/1997 | Purdy |
| 5,695,525 A | 12/1997 | Mulhauser et al. |
| 5,700,285 A | 12/1997 | Myers et al. |
| 5,702,421 A | 12/1997 | Schneidt |
| 5,704,910 A | 1/1998 | Humes |
| 5,709,224 A | 1/1998 | Behl et al. |
| 5,709,704 A | 1/1998 | Nott et al. |
| 5,709,707 A | 1/1998 | Lock et al. |
| 5,722,400 A | 3/1998 | Ockuly et al. |
| 5,724,975 A | 3/1998 | Negus et al. |
| 5,725,512 A | 3/1998 | Swartz et al. |
| 5,725,552 A | 3/1998 | Kotula et al. |
| 5,725,568 A | 3/1998 | Hastings |
| 5,733,294 A | 3/1998 | Forber et al. |
| 5,733,302 A | 3/1998 | Myler et al. |
| 5,735,290 A | 4/1998 | Sterman et al. |
| 5,749,880 A | 5/1998 | Banas et al. |
| 5,749,883 A | 5/1998 | Halpern |
| 5,749,894 A | 5/1998 | Engelson |
| 5,766,219 A | 6/1998 | Horton |
| 5,766,246 A | 6/1998 | Mulhauser et al. |
| 5,769,816 A | 6/1998 | Barbut et al. |
| 5,776,097 A | 7/1998 | Massoud |
| 5,776,162 A | 7/1998 | Kleshinski |
| 5,782,860 A | 7/1998 | Epstein et al. |
| 5,785,679 A | 7/1998 | Abolfathi et al. |
| 5,800,454 A | 9/1998 | Jacobsen et al. |
| 5,800,457 A | 9/1998 | Gelbfish |
| 5,800,512 A | 9/1998 | Letnz et al. |
| 5,807,261 A | 9/1998 | Benaron et al. |
| 5,810,874 A | 9/1998 | Lefebvre |
| 5,814,028 A | 9/1998 | Swartz et al. |
| 5,814,029 A | 9/1998 | Hassett |
| 5,814,064 A | 9/1998 | Daniel |
| 5,820,591 A | 10/1998 | Thompson et al. |

(56) References Cited

U.S. PATENT DOCUMENTS

| | | | |
|---|---|---|---|
| 5,823,198 A | 10/1998 | Jones et al. |
| 5,830,228 A | 11/1998 | Knapp et al. |
| 5,833,673 A | 11/1998 | Ockuly et al. |
| 5,836,913 A | 11/1998 | Orth et al. |
| 5,836,968 A | 11/1998 | Simon et al. |
| 5,840,027 A | 11/1998 | Swartz et al. |
| 5,843,118 A | 12/1998 | Sepetka et al. |
| 5,846,260 A | 12/1998 | Maahs |
| 5,846,261 A | 12/1998 | Kotula et al. |
| 5,848,969 A | 12/1998 | Panescu et al. |
| 5,849,005 A | 12/1998 | Garrison et al. |
| 5,851,232 A | 12/1998 | Lois |
| 5,853,422 A | 12/1998 | Huebsch et al. |
| 5,855,597 A | 1/1999 | Jayaraman |
| 5,865,791 A | 2/1999 | Whayne et al. |
| 5,865,802 A | 2/1999 | Yoon et al. |
| 5,868,702 A | 2/1999 | Stevens et al. |
| 5,868,708 A | 2/1999 | Hart et al. |
| 5,876,367 A | 3/1999 | Kaganov et al. |
| 5,879,296 A | 3/1999 | Ockuly et al. |
| 5,879,366 A | 3/1999 | Shaw et al. |
| 5,882,340 A | 3/1999 | Yoon |
| 5,885,258 A | 3/1999 | Sachdeva et al. |
| 5,891,558 A | 4/1999 | Bell et al. |
| 5,895,399 A | 4/1999 | Barbut et al. |
| 5,902,289 A | 5/1999 | Swartz et al. |
| 5,904,680 A | 5/1999 | Kordis et al. |
| 5,904,703 A | 5/1999 | Gilson |
| 5,906,207 A | 5/1999 | Shen |
| 5,910,154 A | 6/1999 | Tsugita et al. |
| 5,911,734 A | 6/1999 | Tsugita et al. |
| 5,916,236 A | 6/1999 | Muijs Van de Moer et al. |
| 5,925,060 A | 7/1999 | Forber |
| 5,925,063 A | 7/1999 | Khosravi |
| 5,925,074 A | 7/1999 | Gingras et al. |
| 5,925,075 A | 7/1999 | Myers et al. |
| 5,928,192 A | 7/1999 | Maahs |
| 5,928,260 A | 7/1999 | Chin et al. |
| 5,931,818 A | 8/1999 | Werp et al. |
| 5,935,145 A | 8/1999 | Villar et al. |
| 5,935,147 A | 8/1999 | Kensey et al. |
| 5,935,148 A | 8/1999 | Villar et al. |
| 5,941,249 A | 8/1999 | Maynard |
| 5,941,896 A | 8/1999 | Kerr |
| 5,944,738 A | 8/1999 | Amplatz et al. |
| 5,947,997 A | 9/1999 | Pavcnik et al. |
| 5,951,589 A | 9/1999 | Epstein et al. |
| 5,951,599 A | 9/1999 | McCrory |
| 5,954,694 A | 9/1999 | Sunseri |
| 5,954,767 A | 9/1999 | Pajotin et al. |
| 5,957,940 A | 9/1999 | Tanner et al. |
| 5,961,545 A | 10/1999 | Lentz et al. |
| 5,976,174 A | 11/1999 | Ruiz |
| 5,980,514 A | 11/1999 | Kupiecki et al. |
| 5,980,555 A | 11/1999 | Barbut et al. |
| 5,989,281 A | 11/1999 | Barbut et al. |
| 5,993,469 A | 11/1999 | McKenzie et al. |
| 5,993,483 A | 11/1999 | Gianotti |
| 5,997,557 A | 12/1999 | Barbut et al. |
| 6,004,280 A | 12/1999 | Buck et al. |
| 6,004,348 A | 12/1999 | Banas et al. |
| 6,007,523 A | 12/1999 | Mangosong |
| 6,007,557 A | 12/1999 | Ambrisco et al. |
| 6,010,517 A | 1/2000 | Baccaro |
| 6,010,522 A | 1/2000 | Barbut et al. |
| 6,013,093 A | 1/2000 | Nott et al. |
| 6,024,751 A | 2/2000 | Lovato et al. |
| 6,024,754 A | 2/2000 | Engelson |
| 6,024,755 A | 2/2000 | Addis |
| 6,024,756 A | 2/2000 | Huebsch et al. |
| 6,027,520 A | 2/2000 | Tsugita et al. |
| 6,033,420 A | 3/2000 | Hahnen |
| 6,036,720 A | 3/2000 | Abrams et al. |
| 6,042,598 A | 3/2000 | Tsugita et al. |
| 6,048,331 A | 4/2000 | Tsugita et al. |
| 6,051,014 A | 4/2000 | Jang |
| 6,051,015 A | 4/2000 | Maahs |
| 6,056,720 A | 5/2000 | Morse |
| 6,063,070 A | 5/2000 | Eder |
| 6,063,113 A | 5/2000 | Kavteladze et al. |
| 6,066,126 A | 5/2000 | Li et al. |
| 6,068,621 A | 5/2000 | Balceta et al. |
| 6,074,357 A | 6/2000 | Kaganov et al. |
| 6,076,012 A | 6/2000 | Swanson et al. |
| 6,079,414 A | 6/2000 | Roth |
| 6,080,182 A | 6/2000 | Shaw et al. |
| 6,080,183 A | 6/2000 | Tsugita et al. |
| 6,083,239 A | 7/2000 | Addis |
| 6,090,084 A | 7/2000 | Hassett et al. |
| 6,096,052 A | 8/2000 | Callister et al. |
| 6,096,053 A | 8/2000 | Bates et al. |
| 6,110,243 A | 8/2000 | Wnenchak et al. |
| 6,123,715 A | 9/2000 | Amplatz |
| 6,124,523 A | 9/2000 | Banas et al. |
| 6,132,438 A | 10/2000 | Fleischman et al. |
| 6,135,991 A | 10/2000 | Muni et al. |
| 6,136,016 A | 10/2000 | Barbut et al. |
| 6,139,527 A | 10/2000 | Laufer et al. |
| 6,139,573 A | 10/2000 | Sogard et al. |
| 6,152,144 A | 11/2000 | Lesh et al. |
| 6,152,946 A | 11/2000 | Broome et al. |
| 6,156,055 A | 12/2000 | Ravenscroft |
| 6,159,195 A | 12/2000 | Ha et al. |
| 6,161,543 A | 12/2000 | Cox et al. |
| 6,168,615 B1 | 1/2001 | Ken et al. |
| 6,171,329 B1 | 1/2001 | Shaw et al. |
| 6,179,859 B1 | 1/2001 | Bates et al. |
| 6,193,739 B1 | 2/2001 | Chevillon et al. |
| 6,203,531 B1 | 3/2001 | Ockuly et al. |
| 6,206,907 B1 | 3/2001 | Marino et al. |
| 6,214,029 B1 | 4/2001 | Thill et al. |
| 6,221,092 B1 | 4/2001 | Koike et al. |
| 6,231,561 B1 | 5/2001 | Frazier et al. |
| 6,231,589 B1 | 5/2001 | Wessman et al. |
| 6,235,045 B1 | 5/2001 | Barbut et al. |
| 6,245,012 B1 | 6/2001 | Kleshinski |
| 6,251,122 B1 | 6/2001 | Tsukernik |
| 6,258,115 B1 | 7/2001 | Dubrul |
| 6,267,772 B1 | 7/2001 | Mulhauser et al. |
| 6,267,776 B1 | 7/2001 | O'Connell |
| 6,270,490 B1 | 8/2001 | Hahnen |
| 6,270,530 B1 | 8/2001 | Eldridge et al. |
| 6,270,902 B1 | 8/2001 | Tedeschi et al. |
| 6,277,138 B1 | 8/2001 | Levinson et al. |
| 6,285,898 B1 | 9/2001 | Ben-Haim |
| 6,290,674 B1 | 9/2001 | Roue et al. |
| 6,290,708 B1 | 9/2001 | Kugel et al. |
| 6,312,407 B1 | 11/2001 | Zadno-Azizi et al. |
| 6,319,251 B1 | 11/2001 | Tu et al. |
| 6,328,727 B1 | 12/2001 | Frazier et al. |
| 6,328,755 B1 | 12/2001 | Marshall |
| 6,342,062 B1 | 1/2002 | Suon et al. |
| 6,346,116 B1 | 2/2002 | Brooks et al. |
| 6,346,895 B1 | 2/2002 | Lee et al. |
| 6,361,545 B1 | 3/2002 | Macoviak et al. |
| 6,364,895 B1 | 4/2002 | Greenhalgh |
| 6,368,338 B1 | 4/2002 | Kónya et al. |
| 6,371,971 B1 | 4/2002 | Tsugita et al. |
| 6,375,670 B1 | 4/2002 | Greenhalgh |
| 6,391,044 B1 | 5/2002 | Yadav et al. |
| 6,398,803 B1 | 6/2002 | Layne et al. |
| 6,402,746 B1 | 6/2002 | Whayne et al. |
| 6,402,771 B1 | 6/2002 | Palmer et al. |
| 6,402,779 B1 | 6/2002 | Colone et al. |
| 6,419,669 B1 | 7/2002 | Frazier et al. |
| 6,440,152 B1 | 8/2002 | Gainor et al. |
| 6,443,972 B1 | 9/2002 | Bosma et al. |
| 6,447,530 B1 | 9/2002 | Ostrovsky et al. |
| 6,454,775 B1 | 9/2002 | Demarais et al. |
| 6,458,145 B1 | 10/2002 | Ravenscroft et al. |
| 6,464,712 B1 | 10/2002 | Epstein et al. |
| 6,468,291 B2 | 10/2002 | Bates et al. |
| 6,468,301 B1 | 10/2002 | Amplatz et al. |
| 6,485,501 B1 | 11/2002 | Green |

(56) References Cited

U.S. PATENT DOCUMENTS

| | | |
|---|---|---|
| 6,488,689 B1 | 12/2002 | Kaplan et al. |
| 6,511,496 B1 | 1/2003 | Huter et al. |
| 6,514,280 B1 | 2/2003 | Gilson |
| 6,517,573 B1 | 2/2003 | Pollock et al. |
| 6,533,782 B2 | 3/2003 | Howell et al. |
| 6,547,760 B1 | 4/2003 | Samson et al. |
| 6,547,815 B2 | 4/2003 | Myers |
| 6,551,303 B1 | 4/2003 | Van Tassel et al. |
| 6,551,344 B2 | 4/2003 | Thill |
| 6,558,401 B1 | 5/2003 | Azizi |
| 6,558,405 B1 | 5/2003 | McInnes |
| 6,558,414 B2 | 5/2003 | Layne |
| 6,562,058 B2 | 5/2003 | Seguin et al. |
| 6,569,184 B2 | 5/2003 | Huter |
| 6,569,214 B2 | 5/2003 | Williams et al. |
| 6,589,214 B2 | 7/2003 | McGuckin et al. |
| 6,589,251 B2 | 7/2003 | Yee et al. |
| 6,599,308 B2 | 7/2003 | Amplatz |
| 6,602,271 B2 | 8/2003 | Adams et al. |
| 6,623,508 B2 | 9/2003 | Shaw et al. |
| 6,641,564 B1 | 11/2003 | Kraus |
| 6,650,923 B1 | 11/2003 | Lesh et al. |
| 6,652,555 B1 | 11/2003 | VanTassel et al. |
| 6,652,556 B1 | 11/2003 | VanTassel et al. |
| 6,666,861 B1 | 12/2003 | Grabek |
| 6,689,150 B1 | 2/2004 | Vantassel et al. |
| 6,699,260 B2 | 3/2004 | Dubrul et al. |
| 6,699,276 B2 | 3/2004 | Sogard et al. |
| 6,702,825 B2 | 3/2004 | Frazier et al. |
| 6,712,836 B1 | 3/2004 | Berg et al. |
| 6,726,701 B2 | 4/2004 | Gilson et al. |
| 6,730,108 B2 | 5/2004 | Van Tassel et al. |
| 6,755,812 B2 | 6/2004 | Peterson et al. |
| 6,827,737 B2 | 12/2004 | Hill et al. |
| 6,837,901 B2 | 1/2005 | Rabkin et al. |
| 6,855,153 B2 | 2/2005 | Saadat |
| 6,911,037 B2 | 6/2005 | Gainor et al. |
| 6,932,838 B2 | 8/2005 | Schwartz et al. |
| 6,942,653 B2 | 9/2005 | Quinn |
| 6,949,113 B2 | 9/2005 | Van Tassel et al. |
| 6,958,061 B2 | 10/2005 | Truckai et al. |
| 6,994,092 B2 | 2/2006 | van der Burg et al. |
| 7,011,671 B2 | 3/2006 | Welch |
| 7,014,645 B2 | 3/2006 | Greene, Jr. et al. |
| 7,037,321 B2 | 5/2006 | Sachdeva et al. |
| 7,044,134 B2 | 5/2006 | Khairkhahan et al. |
| 7,097,651 B2 | 8/2006 | Harrison et al. |
| 7,128,073 B1 | 10/2006 | van der Burg et al. |
| 7,152,605 B2 | 12/2006 | Khairkhahan et al. |
| 7,169,164 B2 | 1/2007 | Borillo et al. |
| 7,179,275 B2 | 2/2007 | McGuckin, Jr. et al. |
| 7,226,466 B2 | 6/2007 | Opolski |
| 7,303,526 B2 | 12/2007 | Sharkey et al. |
| 7,323,002 B2 | 1/2008 | Johnson et al. |
| 7,597,704 B2 | 10/2009 | Frazier et al. |
| 7,678,123 B2 | 3/2010 | Chanduszko |
| 7,695,425 B2 | 4/2010 | Schweich et al. |
| 7,713,282 B2 | 5/2010 | Frazier et al. |
| 7,722,641 B2 | 5/2010 | van der Burg et al. |
| 7,727,189 B2 | 6/2010 | VanTassel et al. |
| 7,735,493 B2 | 6/2010 | van der Burg et al. |
| 7,780,694 B2 | 8/2010 | Palmer et al. |
| 7,799,049 B2 | 9/2010 | Ostrovsky et al. |
| 7,811,300 B2 | 10/2010 | Feller, III et al. |
| 7,811,314 B2 | 10/2010 | Fierens et al. |
| 7,862,500 B2 | 1/2011 | Khairkhahan et al. |
| 7,927,365 B2 | 4/2011 | Fierens et al. |
| 7,972,359 B2 | 7/2011 | Kreidler |
| 8,025,495 B2 | 9/2011 | Hardert et al. |
| 8,043,329 B2 | 10/2011 | Khairkhahan et al. |
| 8,052,715 B2 | 11/2011 | Quinn et al. |
| 8,062,282 B2 | 11/2011 | Kolb |
| 8,080,032 B2 | 12/2011 | van der Burg et al. |
| 8,097,015 B2 | 1/2012 | Devellian |
| 8,100,938 B2 | 1/2012 | Figulla et al. |
| 8,221,384 B2 | 7/2012 | Frazier et al. |
| 8,221,445 B2 | 7/2012 | van Tassel et al. |
| 8,287,563 B2 | 10/2012 | Khairkhahan et al. |
| 8,323,309 B2 | 12/2012 | Khairkhahan et al. |
| 8,388,672 B2 | 3/2013 | Khairkhahan et al. |
| 8,491,623 B2 | 7/2013 | Vogel et al. |
| 8,523,897 B2 | 9/2013 | van der Burg et al. |
| 8,535,343 B2 | 9/2013 | van der Burg et al. |
| 8,562,509 B2 | 10/2013 | Bates |
| 8,663,273 B2 | 3/2014 | Khairkhahan et al. |
| 8,685,055 B2 | 4/2014 | VanTassel et al. |
| 8,728,117 B1 | 5/2014 | Janardhan et al. |
| 8,758,389 B2 | 6/2014 | Glimsdale |
| 8,828,051 B2 | 9/2014 | Javois et al. |
| 8,834,519 B2 | 9/2014 | van der Burg et al. |
| 8,845,711 B2 | 9/2014 | Miles et al. |
| 9,034,006 B2 | 5/2015 | Quinn et al. |
| 9,132,000 B2 | 9/2015 | VanTassel et al. |
| 9,168,043 B2 | 10/2015 | van der Burg et al. |
| 9,211,124 B2 | 12/2015 | Campbell et al. |
| 9,295,472 B2 | 3/2016 | Ottma |
| 9,351,716 B2 | 5/2016 | Miles et al. |
| 9,445,895 B2 | 9/2016 | Kreidler |
| 9,554,804 B2 | 1/2017 | Erzberger et al. |
| 9,554,806 B2 | 1/2017 | Larsen et al. |
| 9,561,037 B2 | 2/2017 | Fogarty et al. |
| 9,561,097 B1 | 2/2017 | Kim et al. |
| 9,592,058 B2 | 3/2017 | Erzberger et al. |
| 9,597,088 B2 | 3/2017 | Ottma |
| 9,629,636 B2 | 4/2017 | Fogarty et al. |
| 9,730,701 B2 | 8/2017 | Tischler et al. |
| 9,750,505 B2 | 9/2017 | Miles et al. |
| 9,763,666 B2 | 9/2017 | Wu et al. |
| 9,795,387 B2 | 10/2017 | Miles et al. |
| 9,808,253 B2 | 11/2017 | Li et al. |
| 9,883,936 B2 | 2/2018 | Sutton et al. |
| 9,913,652 B2 | 3/2018 | Bridgeman et al. |
| 9,943,299 B2 | 4/2018 | Khairkhahan et al. |
| 9,943,315 B2 | 4/2018 | Kaplan et al. |
| 10,071,181 B1 | 9/2018 | Penegor et al. |
| 10,076,335 B2 | 9/2018 | Zaver et al. |
| 10,143,458 B2 | 12/2018 | Kreidler |
| 10,201,337 B2 | 2/2019 | Glimsdale |
| 10,231,737 B2 | 3/2019 | Amplatz et al. |
| 2001/0000797 A1 | 5/2001 | Mazzocchi |
| 2001/0020181 A1 | 9/2001 | Layne |
| 2001/0034537 A1 | 10/2001 | Shaw et al. |
| 2001/0037141 A1 | 11/2001 | Yee et al. |
| 2002/0022860 A1 | 2/2002 | Borillo et al. |
| 2002/0035374 A1 | 3/2002 | Borillo et al. |
| 2002/0045931 A1 | 4/2002 | Sogard et al. |
| 2002/0062133 A1 | 5/2002 | Gilson et al. |
| 2002/0082638 A1 | 6/2002 | Porter et al. |
| 2002/0082675 A1 | 6/2002 | Myers |
| 2002/0099439 A1 | 7/2002 | Schwartz et al. |
| 2002/0111647 A1 | 8/2002 | Khairkhahan et al. |
| 2002/0138094 A1 | 9/2002 | Borillo et al. |
| 2002/0138097 A1 | 9/2002 | Ostrovsky et al. |
| 2002/0169475 A1 | 11/2002 | Gainor et al. |
| 2002/0177855 A1 | 11/2002 | Greene, Jr. et al. |
| 2003/0017775 A1 | 1/2003 | Dong et al. |
| 2003/0023262 A1 | 1/2003 | Welch |
| 2003/0023266 A1 | 1/2003 | Borillo et al. |
| 2003/0057156 A1 | 3/2003 | Peterson et al. |
| 2003/0060871 A1 | 3/2003 | Hill et al. |
| 2003/0120337 A1 | 6/2003 | Van Tassel et al. |
| 2003/0181942 A1 | 9/2003 | Sutton et al. |
| 2003/0191526 A1 | 10/2003 | Van Tassel et al. |
| 2003/0195555 A1 | 10/2003 | Khairkhahan et al. |
| 2003/0204203 A1 | 10/2003 | Khairkhahan et al. |
| 2003/0208214 A1 | 11/2003 | Loshakove et al. |
| 2003/0220667 A1 | 11/2003 | van der Burg et al. |
| 2004/0034366 A1 | 2/2004 | van der Burg et al. |
| 2004/0049210 A1 | 3/2004 | VanTassel et al. |
| 2004/0093012 A1 | 5/2004 | Cully et al. |
| 2004/0098031 A1 | 5/2004 | van der Burg et al. |
| 2004/0122467 A1 | 6/2004 | VanTassel et al. |
| 2004/0127935 A1 | 7/2004 | VanTassel et al. |
| 2004/0158274 A1 | 8/2004 | WasDyke |

(56) References Cited

U.S. PATENT DOCUMENTS

| | | |
|---|---|---|
| 2004/0186486 A1 | 9/2004 | Roue et al. |
| 2004/0215230 A1 | 10/2004 | Frazier et al. |
| 2004/0220610 A1 | 11/2004 | Kreidler et al. |
| 2004/0220682 A1 | 11/2004 | Levine et al. |
| 2004/0230222 A1 | 11/2004 | van der Burg et al. |
| 2005/0004652 A1 | 1/2005 | van der Burg et al. |
| 2005/0015109 A1 | 1/2005 | Lichtenstein |
| 2005/0038470 A1 | 2/2005 | van der Burg et al. |
| 2005/0049573 A1 | 3/2005 | Van Tassel et al. |
| 2005/0070952 A1 | 3/2005 | Devellian |
| 2005/0113861 A1 | 5/2005 | Corcoran et al. |
| 2005/0125020 A1 | 6/2005 | Meade et al. |
| 2005/0177182 A1 | 8/2005 | van der Burg et al. |
| 2005/0203568 A1 | 9/2005 | Burg et al. |
| 2005/0283186 A1 | 12/2005 | Berrada et al. |
| 2005/0288704 A1 | 12/2005 | Cartier et al. |
| 2006/0015136 A1 | 1/2006 | Besselink |
| 2006/0030877 A1 | 2/2006 | Martinez et al. |
| 2006/0052816 A1 | 3/2006 | Bates et al. |
| 2006/0100658 A1 | 5/2006 | Obana et al. |
| 2006/0155323 A1 | 7/2006 | Porter et al. |
| 2007/0066993 A1 | 3/2007 | Kreidler |
| 2007/0083227 A1 | 4/2007 | van der Burg et al. |
| 2007/0083230 A1 | 4/2007 | Javois |
| 2007/0150041 A1 | 6/2007 | Evans et al. |
| 2007/0156123 A1 | 7/2007 | Moll et al. |
| 2007/0162048 A1 | 7/2007 | Quinn et al. |
| 2007/0185471 A1 | 8/2007 | Johnson |
| 2008/0275536 A1 | 11/2008 | Zarins et al. |
| 2009/0005803 A1 | 1/2009 | Batiste |
| 2009/0062841 A1 | 3/2009 | Amplatz et al. |
| 2009/0099647 A1 | 4/2009 | Glimsdale et al. |
| 2009/0105747 A1 | 4/2009 | Chanduszko et al. |
| 2009/0112249 A1 | 4/2009 | Miles et al. |
| 2009/0254195 A1 | 10/2009 | Khairkhan et al. |
| 2009/0318948 A1 | 12/2009 | Linder et al. |
| 2010/0004726 A1 | 1/2010 | Hancock et al. |
| 2010/0049238 A1 | 2/2010 | Simpson |
| 2010/0106178 A1 | 4/2010 | Obermiller et al. |
| 2010/0324585 A1 | 12/2010 | Miles et al. |
| 2011/0054515 A1* | 3/2011 | Bridgeman ...... A61B 17/12122 |
| | | 606/200 |
| 2011/0082495 A1 | 4/2011 | Ruiz |
| 2011/0098525 A1 | 4/2011 | Kermode et al. |
| 2011/0218566 A1 | 9/2011 | van der Burg et al. |
| 2011/0301630 A1 | 12/2011 | Hendriksen et al. |
| 2012/0029553 A1 | 2/2012 | Quinn et al. |
| 2012/0035643 A1 | 2/2012 | Khairkhahan et al. |
| 2012/0065662 A1 | 3/2012 | van der Burg et al. |
| 2012/0125619 A1 | 5/2012 | Wood et al. |
| 2012/0172654 A1 | 7/2012 | Bates |
| 2012/0172927 A1 | 7/2012 | Campbell et al. |
| 2012/0239077 A1 | 9/2012 | Zaver et al. |
| 2012/0239083 A1 | 9/2012 | Kreidler |
| 2012/0245619 A1 | 9/2012 | Guest |
| 2012/0283585 A1 | 11/2012 | Werneth et al. |
| 2012/0283773 A1 | 11/2012 | Van Tassel et al. |
| 2012/0323267 A1 | 12/2012 | Ren |
| 2013/0006343 A1 | 1/2013 | Kassab et al. |
| 2013/0012982 A1 | 1/2013 | Khairkhahan et al. |
| 2013/0018413 A1 | 1/2013 | Oral et al. |
| 2013/0110154 A1 | 5/2013 | van der Burg et al. |
| 2013/0165735 A1 | 6/2013 | Khairkhahan et al. |
| 2013/0211492 A1 | 8/2013 | Schneider et al. |
| 2013/0331884 A1 | 12/2013 | Van der Burg et al. |
| 2014/0005714 A1 | 1/2014 | Quick et al. |
| 2014/0018841 A1 | 1/2014 | Peiffer et al. |
| 2014/0039536 A1 | 2/2014 | Cully et al. |
| 2014/0046360 A1 | 2/2014 | van der Burg et al. |
| 2014/0081314 A1 | 3/2014 | Zaver et al. |
| 2014/0100596 A1 | 4/2014 | Rudman et al. |
| 2014/0135817 A1* | 5/2014 | Tischler .......... A61B 17/12122 |
| | | 29/428 |
| 2014/0142612 A1 | 5/2014 | Li et al. |
| 2014/0148842 A1 | 5/2014 | Khairkhahan et al. |
| 2014/0163605 A1 | 6/2014 | VanTassel et al. |
| 2014/0188157 A1 | 7/2014 | Clark |
| 2014/0214077 A1 | 7/2014 | Glimsdale |
| 2014/0296908 A1 | 10/2014 | Ottma et al. |
| 2014/0303719 A1 | 10/2014 | Cox et al. |
| 2014/0336612 A1 | 11/2014 | Frydlewski et al. |
| 2014/0336699 A1 | 11/2014 | van der Burg et al. |
| 2015/0005810 A1 | 1/2015 | Center et al. |
| 2015/0039021 A1 | 2/2015 | Khairkhahan et al. |
| 2015/0080903 A1 | 3/2015 | Dillard et al. |
| 2015/0196300 A1 | 7/2015 | Tischler et al. |
| 2015/0230909 A1 | 8/2015 | Zaver et al. |
| 2015/0238197 A1 | 8/2015 | Quinn et al. |
| 2015/0305727 A1 | 10/2015 | Karimov et al. |
| 2015/0313604 A1 | 11/2015 | Roue et al. |
| 2015/0313605 A1 | 11/2015 | Griffin |
| 2015/0327979 A1 | 11/2015 | Quinn et al. |
| 2015/0374491 A1 | 12/2015 | Kreidler |
| 2016/0015397 A1 | 1/2016 | Figulla et al. |
| 2016/0051358 A1 | 2/2016 | Sutton et al. |
| 2016/0058539 A1 | 3/2016 | VanTassel et al. |
| 2016/0066922 A1 | 3/2016 | Bridgeman et al. |
| 2016/0106437 A1 | 4/2016 | van der Burg et al. |
| 2016/0192942 A1 | 7/2016 | Strauss et al. |
| 2016/0287259 A1 | 10/2016 | Hanson et al. |
| 2016/0331382 A1 | 11/2016 | Center et al. |
| 2016/0374657 A1 | 12/2016 | Kreidler |
| 2017/0007262 A1 | 1/2017 | Amplatz et al. |
| 2017/0027552 A1 | 2/2017 | Turkington et al. |
| 2017/0042550 A1 | 2/2017 | Chakraborty et al. |
| 2017/0056166 A1 | 3/2017 | Ratz et al. |
| 2017/0100112 A1 | 4/2017 | van der Burg et al. |
| 2017/0119400 A1 | 5/2017 | Amplatz et al. |
| 2017/0181751 A1 | 6/2017 | Larsen et al. |
| 2017/0224354 A1 | 8/2017 | Tischler et al. |
| 2017/0340336 A1 | 11/2017 | Osypka |
| 2017/0354421 A1 | 12/2017 | Maguire et al. |
| 2018/0064446 A1 | 3/2018 | Figulla et al. |
| 2018/0070950 A1 | 3/2018 | Zaver et al. |
| 2018/0140412 A1 | 5/2018 | Sutton et al. |
| 2018/0140413 A1 | 5/2018 | Quinn et al. |
| 2018/0250014 A1 | 9/2018 | Melanson et al. |
| 2019/0133563 A1 | 5/2019 | Glimsdale |
| 2019/0175185 A1 | 6/2019 | Amplatz et al. |
| 2019/0223883 A1 | 7/2019 | Anderson et al. |
| 2019/0247053 A1 | 8/2019 | Inouye |
| 2019/0298380 A1* | 10/2019 | Inouye ............. A61B 17/12031 |
| 2021/0059685 A1 | 3/2021 | Groff et al. |

FOREIGN PATENT DOCUMENTS

| | | | |
|---|---|---|---|
| CN | 104287804 A | | 1/2015 |
| CN | 104352261 A | | 2/2015 |
| CN | 106859722 A | | 6/2017 |
| CN | 109464173 A | | 3/2019 |
| DE | 10201004476 A1 | | 3/2012 |
| EP | 1523957 A2 | | 4/2005 |
| EP | 1595504 A1 | | 11/2005 |
| EP | 2074953 A1 | | 1/2009 |
| EP | 2481381 A1 | | 8/2012 |
| EP | 2928420 A1 | | 10/2015 |
| EP | 3072461 A1 | | 9/2016 |
| EP | 3372173 A2 | | 9/2018 |
| EP | 3398523 A1 | | 11/2018 |
| JP | 2003532457 A | | 11/2003 |
| JP | 2005324019 A | | 11/2005 |
| JP | 2007513684 A | | 5/2007 |
| JP | 2009160402 A | | 7/2009 |
| JP | 2012501793 A | | 1/2012 |
| WO | 9313712 A1 | | 7/1993 |
| WO | 9504132 A1 | | 2/1995 |
| WO | 9522359 A1 | | 8/1995 |
| WO | 9601591 A1 | | 1/1996 |
| WO | 9640356 A1 | | 12/1996 |
| WO | 9721402 A1 | | 6/1997 |
| WO | 9726939 A1 | | 7/1997 |
| WO | 9728749 A1 | | 8/1997 |
| WO | 9735522 A1 | | 10/1997 |
| WO | 9802100 A1 | | 1/1998 |

(56)                References Cited

FOREIGN PATENT DOCUMENTS

| WO | 9817187 A1 | 4/1998 |
|---|---|---|
| WO | 9822026 A1 | 5/1998 |
| WO | 9823322 A1 | 6/1998 |
| WO | 9827868 A1 | 7/1998 |
| WO | 9905977 A1 | 2/1999 |
| WO | 9907289 A1 | 2/1999 |
| WO | 9908607 A1 | 2/1999 |
| WO | 9923976 A1 | 5/1999 |
| WO | 9925252 A1 | 5/1999 |
| WO | 9930640 A1 | 6/1999 |
| WO | 9944510 A1 | 9/1999 |
| WO | 9959479 A1 | 11/1999 |
| WO | 0001308 A1 | 1/2000 |
| WO | 0016705 A1 | 3/2000 |
| WO | 0027292 A1 | 5/2000 |
| WO | 0035352 A1 | 6/2000 |
| WO | 0053120 A1 | 9/2000 |
| WO | 0067669 A1 | 11/2000 |
| WO | 0108743 A1 | 2/2001 |
| WO | 0115629 A1 | 3/2001 |
| WO | 0121247 A1 | 3/2001 |
| WO | 0126726 A1 | 4/2001 |
| WO | 0130266 A1 | 5/2001 |
| WO | 0130267 A1 | 5/2001 |
| WO | 0130268 A1 | 5/2001 |
| WO | 0170119 A1 | 9/2001 |
| WO | 0215793 A2 | 2/2002 |
| WO | 0224106 A2 | 3/2002 |
| WO | 02071977 A2 | 9/2002 |
| WO | 03007825 A1 | 1/2003 |
| WO | 03008030 A2 | 1/2003 |
| WO | 03032818 A1 | 4/2003 |
| WO | 2004012629 A1 | 2/2004 |
| WO | 2007044536 A1 | 4/2007 |
| WO | 2010024801 A1 | 3/2010 |
| WO | 2010081033 A1 | 7/2010 |
| WO | 2013060855 A1 | 5/2013 |
| WO | 2013159065 A1 | 10/2013 |
| WO | 2014011865 A1 | 1/2014 |
| WO | 2014018907 A1 | 1/2014 |
| WO | 2014089129 A1 | 6/2014 |
| WO | 201406239 A1 | 7/2014 |
| WO | 2015164836 A1 | 10/2015 |
| WO | 2016087145 A1 | 6/2016 |
| WO | 2018017935 A1 | 1/2018 |
| WO | 2018187732 A1 | 10/2018 |
| WO | 2019084358 A1 | 5/2019 |

OTHER PUBLICATIONS

International Search Report and Written Opinion dated Feb. 15, 2000 for International Application No. PCT/US99/26325.
International Search Report dated May 20, 2003 for International Application No. PCT/US02/33808.
Written Opinion dated Nov. 17, 2003 for International Application No. PCT/US/02/33808.
International Search Report and Written Opinion dated Aug. 21, 2018 for International Application No. PCT/US2018/029684.
Cragg et al., "A New Percutaneous Vena Cava Filter," American Journal of Radiology, Sep. 1983, pp. 601-604, vol. 141.
Cragg et al., "Nonsurgical Placement of Arterial Endoprostheses: A New Technique Using Nitinol Wire," Radiology, Apr. 1983, pp. 261-263, vol. 147, No. 1.
Lock et al., "Transcatheter Closure of Atrial Septal Defects." Circulation, May 1989, pp. 1091-1099, vol. 79, No. 5.

Lock et al., "Transcatheter Umbrella Closure of Congenital Heart Defects," Circulation, Mar. 1987, pp. 593-599, vol. 75, No. 3.
Rashkind et al., "Nonsurgical closure of patent ductus arteriosus: clinical application of the Rashkind PDA Occluder System," Circulation, Mar. 1987, pp. 583-592, vol. 75, No. 3.
Rosengart et al., "Percutaneous and Minimally Invasive Valve Procedures," Circulation, Apr. 1, 2008, pp. 1750-1767, vol. 117.
Ruttenberg, "Nonsurgical Therapy of Cardiac Disorders," Pediatric Consult, 1986, Pages not numbered, vol. 5, No. 2.
Sugita et al., "Nonsurgical Implantations of a Vascular Ring Prosthesis Using Thermal Shape Memory Ti/Ni Alloy (Nitinol Wire)," Trans. Am. Soc. Artif. Intern. Organs, 1986, pp. 30-34, vol. XXXII.
Wessel et al., "Outpatient Closure of the Patent Ductus Arteriousus," Circulation, 1988, pp. 1068-1071, vol. 77, No. 5.
Tung et al., U.S. Appl. No. 61/559,941, filed Nov. 15, 2011.
Yue Yu et al., U.S. Appl. No. 61/557,880, filed Dec. 20, 2011.
Cline, "File: Fish hooks.jpg," Wikipedia foundation , Inc., San Francisco, CA, Jun. 2007; p. 1 of 4; available online at http://en.wikipedia.org/wiki/File:Fish_hooks.jpg; last accessed Oct. 5, 2012.
International Search Report and Written Opinion dated Apr. 22, 2014 for International Application No. PCT/US2013/078454.
Aryana et al., "Incomplete Closure of the Left Atrial Appendage: Implication and Management." Curr Cardiol Rep., 18(9):82, 2016.
Delurgio, "Device-Associated Thrombus and Peri-Device Leak Following Left Atrial Appendage Closure with the Amplatzer Cardiac Plug." JACC: Cardiovascular Interventions, 10(4): 400-402, 2017.
University of Minnesota. Atlas of Human Cardiac Anatomy, Left Atrium. Retrieved from http://www.vhlab.umn.edu/atlas/left-atrium/left-atrial-appendage/index.shtml. Accessed 2017. Downloaded 2019.
Saw et al., "Incidence and Clinical Impact of Device-Associated Thrombus and Peri-Device Leak following Left Atrial Appendage Closure with the Amplatzer Cardiac Plug." JACC: Cardiovascular Intervention. 10(4): 391-399, 2017.
Romero et al., "Left Atrial Appendage Closure Devices," Clinical Medicine Insights: Cardiology, vol. 8, pp. 45-52, 2014.
Invitation To Pay Additional Fees And, Where Applicable, Protest Fee, mailed Oct. 13, 2016.
International Search Report and Written Opinion dated Oct. 14, 2019 for International Application No. PCT/US2019/047452.
International Search Report and Written Opinion dated Oct. 27, 2017 for International Application No. PCT/US2017/048150.
International Search Report and Written Opinion dated Jan. 21, 2019 for International Application No. PCT/US2018/051953.
International Search Report and Written Opinion dated Oct. 13, 2016 for International Application No. PCT/US2016/043363.
International Search Report and Written Opinion dated Mar. 17, 2020, for International Application No. PCT/US2019/065243.
International Search Report and Written Opinion dated Sep. 9, 2019 for International Application No. PCT/US2019/033698.
Blackshear et al; "Appendage Obliteration to Reduce Stroke in Cardiac Surgical Patients with Atrial Fibrillation", Ann. Thoracic Surgery, pp. 755-759, 1996.
Lindsay, "Obliteration of the Left Atrial Appendage: A Concept Worth Testing", Ann. Thoracic Surgery, 1996.
Invitation To Pay Additional Fees dated Feb. 22, 2019 for International Application No. PCT/US2018/066163.
International Search Report and Written Opinion dated Oct. 20, 2020 for International Application No. PCT/US2020/042192.
International Search Report and Written Opinion dated Oct. 23, 2020 for International Application No. PCT/US2020/048437.
Watchman FLX™ Left Atrial Appendage Closure Device, Boston Scientific. 5 pages, 2022.
International Search Report and Written Opinion dated Oct. 25, 2022 for International Application No. PCT/US2022/036092.

* cited by examiner

LEFT ATRIAL APPENDAGE CLOSURE DEVICE

CROSS-REFERENCE TO RELATED APPLICATIONS

This application is a continuation of U.S. application Ser. No. 17/857,513, filed Jul. 5, 2022, which claims the benefit of priority of U.S. Provisional Application No. 63/219,696 filed Jul. 8, 2021, the entire disclosure of which is hereby incorporated by reference.

TECHNICAL FIELD

The disclosure relates generally to medical devices and more particularly to medical devices that are adapted for use in percutaneous medical procedures including implantation into the left atrial appendage (LAA) of a heart.

BACKGROUND

The left atrial appendage is a small organ attached to the left atrium of the heart. During normal heart function, as the left atrium constricts and forces blood into the left ventricle, the left atrial appendage constricts and forces blood into the left atrium. The ability of the left atrial appendage to contract assists with improved filling of the left ventricle, thereby playing a role in maintaining cardiac output. However, in patients suffering from atrial fibrillation, the left atrial appendage may not properly contract or empty, causing stagnant blood to pool within its interior, which can lead to the undesirable formation of thrombi within the left atrial appendage.

Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation originate in the left atrial appendage. As a treatment, medical devices have been developed which are deployed to close off the left atrial appendage. Of the known medical devices and methods, each has certain advantages and disadvantages. There is an ongoing need to provide alternative medical devices and introducers as well as alternative methods for manufacturing and using medical devices and introducers.

SUMMARY

In one example, a left atrial appendage closure device may comprise an expandable framework having a plurality of struts disposed about a central longitudinal axis, the plurality of struts being joined together at a proximal hub and a distal hub. When the expandable framework is fully constrained in a first position by a delivery sheath, a first segment of the plurality of struts extends distally from the distal hub parallel to the central longitudinal axis to a first bend and a second segment of the plurality of struts extends from the first bend proximally. A first amount of the expandable framework is unconstrained by the delivery sheath in a second position. In the second position the first segment of the plurality of struts extends distally from the distal hub parallel to the central longitudinal axis to the first bend, the second segment of the plurality of struts extends from the first bend proximally and radially outward to a second bend, a third segment of the plurality of struts extends from the second bend proximally and radially inward to a third bend, and a fourth segment of the plurality of struts extends from the third bend proximally to within the delivery sheath.

In addition or alternatively to any example disclosed herein, in the second position the first segment and the second segment form an acute angle opening inwardly toward an interior of the expandable framework.

In addition or alternatively to any example disclosed herein, a second amount of the expandable framework greater than the first amount is unconstrained by the delivery sheath in a third position. In the third position the first segment of the plurality of struts extends distally from the distal hub parallel to the central longitudinal axis to the first bend, the second segment of the plurality of struts extends from the first bend radially outward generally perpendicular to the central longitudinal axis to the second bend, the third segment of the plurality of struts extends from the second bend proximally and radially inward to the third bend, and the fourth segment of the plurality of struts extends from the third bend proximally toward the proximal hub disposed within the delivery sheath.

In addition or alternatively to any example disclosed herein, in the third position the second segment and the third segment form an acute angle opening inwardly toward the central longitudinal axis.

In addition or alternatively to any example disclosed herein, in the third position the third segment and the fourth segment form an obtuse angle opening outwardly away from the central longitudinal axis.

In addition or alternatively to any example disclosed herein, a third amount of the expandable framework greater than the second amount is unconstrained by the delivery sheath in a fourth position. In the fourth position the first segment of the plurality of struts extends distally from the distal hub parallel to the central longitudinal axis to the first bend, the second segment of the plurality of struts extends from the first bend distally and radially outward to the second bend, the third segment of the plurality of struts extends from the second bend proximally and radially inward toward the third bend, and the fourth segment of the plurality of struts extends from the third bend proximally toward the proximal hub disposed within the delivery sheath.

In addition or alternatively to any example disclosed herein, in the fourth position the first segment and the second segment form an obtuse angle opening inwardly toward an interior of the expandable framework.

In addition or alternatively to any example disclosed herein, in the fourth position the second segment and the third segment form an acute angle opening inwardly toward the central longitudinal axis.

In addition or alternatively to any example disclosed herein, in the fourth position the third segment and the fourth segment form an obtuse angle opening outwardly away from the central longitudinal axis.

In addition or alternatively to any example disclosed herein, a fourth amount of the expandable framework greater than the third amount is unconstrained by the delivery sheath in a fifth position. In the fifth position the first segment of the plurality of struts extends distally from the distal hub parallel to the central longitudinal axis to the first bend, the second segment of the plurality of struts extends from the first bend distally and radially outward to the second bend, the third segment of the plurality of struts extends from the second bend proximally to the third bend, and the fourth segment of the plurality of struts extends from the third bend radially inward toward the proximal hub.

In addition or alternatively to any example disclosed herein, in the fifth position the first segment and the second segment form an obtuse angle opening inwardly.

In addition or alternatively to any example disclosed herein, in the fifth position the second segment and the third segment form an acute angle opening inwardly.

In addition or alternatively to any example disclosed herein, in the fifth position the third segment and the fourth segment form an angle of about 90 degrees or less opening inwardly.

In addition or alternatively to any example disclosed herein, the distal hub is disposed proximal of the first bend.

In addition or alternatively to any example disclosed herein, in the second position the distal hub is disposed distal of the second bend.

In addition or alternatively to any example disclosed herein, a left atrial appendage closure device may comprise an expandable framework having a plurality of struts disposed about a central longitudinal axis, the plurality of struts being joined together at a proximal hub and a distal hub. As the expandable framework shifts from fully constrained to fully unconstrained, the expandable framework transitions sequentially through a plurality of positions. In a first position, a first segment of the plurality of struts extends distally from the distal hub parallel to the central longitudinal axis to a first bend and a second segment of the plurality of struts extends from the first bend proximally and generally parallel to the central longitudinal axis. In a second position, the second segment of the plurality of struts, if swept circumferentially around the central longitudinal axis, defines a generally conical shape tapering radially outward in a proximal direction from the first bend toward a second bend.

In addition or alternatively to any example disclosed herein, in the second position, the distal hub is disposed proximal of the first bend and the distal hub is disposed distal of the second bend.

In addition or alternatively to any example disclosed herein, in a third position, the second segment of the plurality of struts, if swept circumferentially around the central longitudinal axis, defines a generally planar shape oriented generally perpendicular to the central longitudinal axis.

In addition or alternatively to any example disclosed herein, in a fourth position, the second segment of the plurality of struts, if swept circumferentially around the central longitudinal axis, defines a generally conical shape tapering radially outward in a distal direction from the first bend toward the second bend.

In addition or alternatively to any example disclosed herein, a left atrial appendage closure device system may comprise a delivery sheath having a lumen extending therein, and a left atrial appendage closure device comprising an expandable framework having a plurality of struts disposed about a central longitudinal axis, the plurality of struts being joined together at a proximal hub and a distal hub. When the expandable framework is disposed within the lumen of the delivery sheath in a first position, a first segment of the plurality of struts extends distally from the distal hub parallel to the central longitudinal axis to a first bend and a second segment of the plurality of struts extends from the first bend proximally. Relative axial translation between the delivery sheath and the expandable framework exposes some of the expandable framework in a second position. In the second position the first segment of the plurality of struts extends distally from the distal hub parallel to the central longitudinal axis to the first bend, the second segment of the plurality of struts extends from the first bend proximally and radially outward to a second bend, a third segment of the plurality of struts extends from the second bend proximally and radially inward to a third bend, and a fourth segment of the plurality of struts extends from the third bend proximally to within the delivery sheath. Relative axial translation between the delivery sheath and the expandable framework exposes more of the expandable framework in a third position than in the second position. In the third position the first segment of the plurality of struts extends distally from the distal hub parallel to the central longitudinal axis to the first bend, the second segment of the plurality of struts extends from the first bend radially outward generally perpendicular to the central longitudinal axis to the second bend, the third segment of the plurality of struts extends from the second bend proximally and radially inward to the third bend, and the fourth segment of the plurality of struts extends from the third bend proximally toward the proximal hub disposed within the delivery sheath. Relative axial translation between the delivery sheath and the expandable framework exposes more of the expandable framework in a fourth position than in the third position. In the fourth position the first segment of the plurality of struts extends distally from the distal hub parallel to the central longitudinal axis to the first bend, the second segment of the plurality of struts extends from the first bend distally and radially outward to the second bend, the third segment of the plurality of struts extends from the second bend proximally and radially inward toward the third bend, and the fourth segment of the plurality of struts extends from the third bend proximally toward the proximal hub disposed within the delivery sheath. Relative axial translation between the delivery sheath and the expandable framework exposes all of the expandable framework in a fifth position. In the fifth position the first segment of the plurality of struts extends distally from the distal hub parallel to the central longitudinal axis to the first bend, the second segment of the plurality of struts extends from the first bend distally and radially outward to the second bend, the third segment of the plurality of struts extends from the second bend proximally to the third bend, and the fourth segment of the plurality of struts extends from the third bend radially inward toward the proximal hub.

The above summary of some embodiments, aspects, and/or examples is not intended to describe each embodiment or every implementation of the present disclosure. The figures and the detailed description more particularly exemplify aspects of these embodiments.

BRIEF DESCRIPTION OF THE DRAWINGS

The disclosure may be more completely understood in consideration of the following detailed description in connection with the accompanying drawings, in which.

Figure 1:
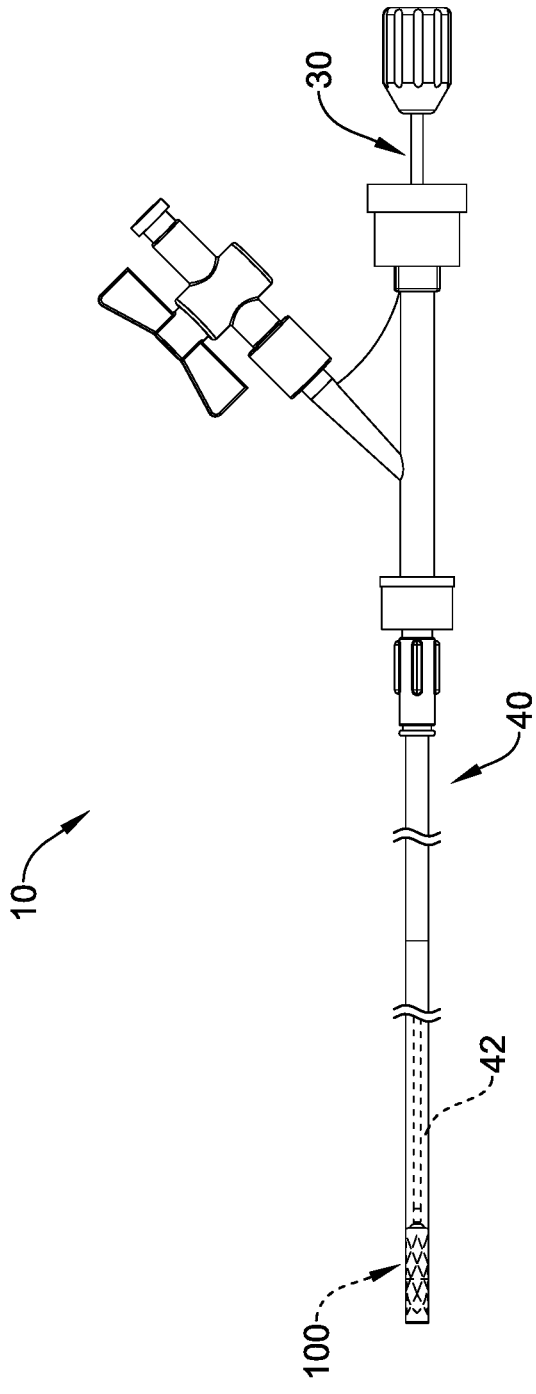
FIGS. 1-2 are side views of a left atrial appendage closure device system.

While aspects of the disclosure are amenable to various modifications and alternative forms, examples are shown in the drawings and described herein. It should be understood, however, that the intention is not to limit aspects of the disclosure to the particular embodiments described. On the contrary, the disclosure shall cover all modifications, equivalents, and alternatives falling within the spirit and scope thereof.

DETAILED DESCRIPTION

The following description should be read with reference to the drawings, which are not necessarily to scale, wherein like reference numerals indicate like elements throughout the several views. The detailed description and drawings are intended to illustrate but not limit the present disclosure. Those skilled in the art will recognize that the various elements described and/or shown may be arranged in various combinations and configurations without departing from the scope of the disclosure. The detailed description and drawings illustrate exemplary aspects of the disclosure. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, all elements of the present disclosure are not necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean the greatest measurement of a stated or identified dimension, unless the extent or dimension in question is preceded by or identified as a "minimum", which may be understood to mean the smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered the greatest possible dimension measured according to the intended usage, while a "minimum extent" may be considered the smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The left atrial appendage may be attached to and in fluid communication with a left atrium of a patient's heart. In some patients, the left atrial appendage may have a complex geometry and/or irregular surface area. Those of skill in the art will also recognize that the medical devices and methods disclosed herein may be adapted for various sizes and shapes of the left atrial appendage, as necessary. The left atrial appendage may include a generally longitudinal axis arranged along a depth of a main body of the left atrial appendage. The main body may include a wall and an ostium forming a proximal mouth. In some embodiments, a lateral extent of the ostium and/or the wall may be smaller or less than a depth of the main body along the longitudinal axis, or a depth of the main body may be greater than a lateral extent of the ostium and/or the wall. In some embodiments, the left atrial appendage may include a tail-like element associated with a distal portion of the main body, which element may protrude radially or laterally away from the main body.

The following figures illustrate selected components and/ or arrangements of a left atrial appendage closure device, a left atrial appendage closure device system, and/or methods of using the left atrial appendage closure device and/or the left atrial appendage closure device system. It should be noted that in any given figure, some features may not be shown, or may be shown schematically, for simplicity. Additional details regarding some of the components of the implant and/or the system may be illustrated in other figures in greater detail. While discussed in the context of occluding the left atrial appendage, the left atrial appendage closure device and/or the left atrial appendage closure device system may also be used for other interventions and/or percutaneous medical procedures within a patient. Similarly, the devices and methods described herein with respect to percutaneous deployment may be used in other types of surgical procedures, as appropriate. For example, in some examples, the devices may be used in a non-percutaneous procedure. Devices and methods in accordance with the disclosure may also be adapted and configured for other uses within the anatomy.

Figure 2:
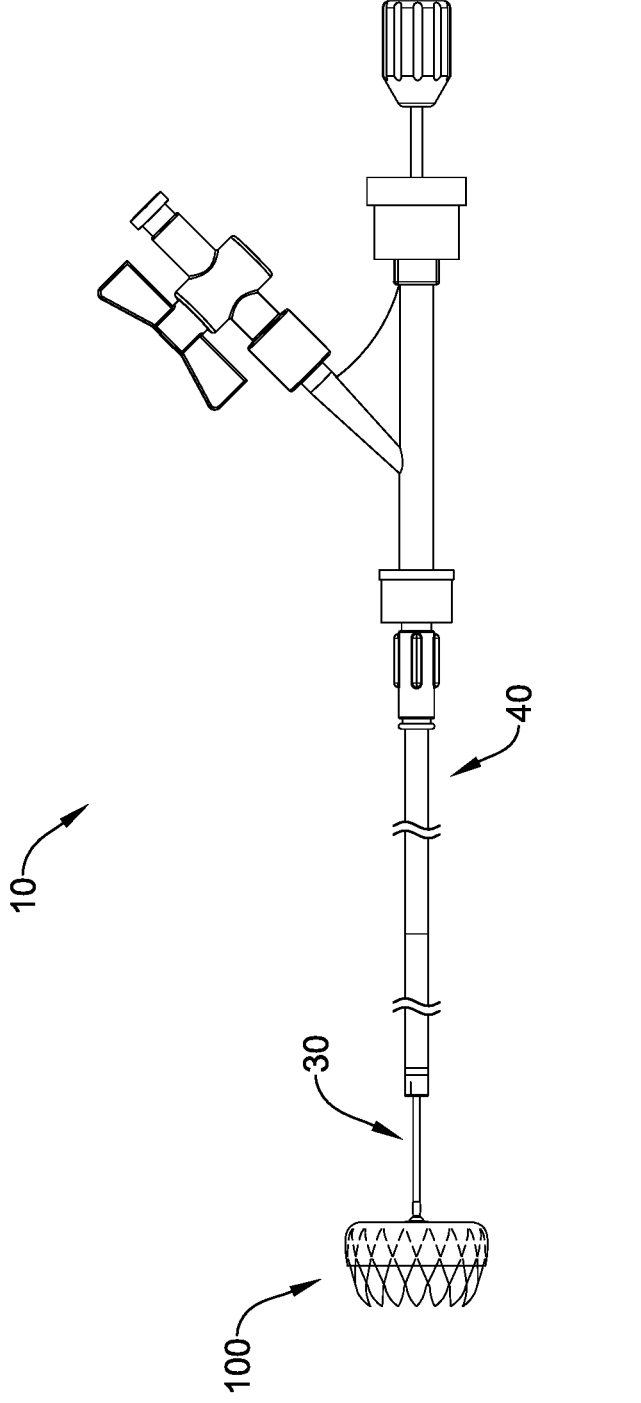

FIGS. 1-2 illustrate selected components and/or arrangements of a left atrial appendage closure device system 10 which may be used for occluding a left atrial appendage. It should be noted that in any given figure, some features of the left atrial appendage closure device system 10 may not be shown, or may be shown schematically, for simplicity. Additional details regarding some of the components of the left atrial appendage closure device system 10 may be illustrated in other figures in greater detail.

The left atrial appendage closure device system 10 may include a delivery sheath 40 having a lumen 42 extending from a proximal opening to a distal opening, a core wire 30 slidably disposed within the lumen 42, and a left atrial appendage closure device 100 for occluding the left atrial appendage. The left atrial appendage closure device 100 may include an expandable framework 110 (e.g., FIG. 3) configured to shift between a fully constrained configuration (e.g., FIG. 1), wherein the left atrial appendage closure device 100 is disposed within the lumen 42 proximate the distal opening in the delivery configuration, and a fully unconstrained configuration (e.g., FIG. 2), wherein the left atrial appendage closure device 100 and/or the expandable framework 110 is configured to shift between the fully constrained configuration and the fully unconstrained configuration as the left atrial appendage closure device 100 is translated relative to the delivery sheath 40. In at least some embodiments, the expandable framework 110 may be self-biased toward the fully unconstrained configuration.

The left atrial appendage closure device 100 may be disposed at and/or releasably securable to a distal portion of the core wire 30. The core wire 30 may be slidably and/or rotatably disposed within the lumen 42 of the delivery sheath 40. In some embodiments, a proximal end of the core wire 30 may extend proximally of a proximal end of the delivery sheath 40 and/or the proximal opening of the lumen 42 for manual manipulation by a clinician or practitioner. In some embodiments, the left atrial appendage closure device 100 may be removably attached, joined, secured, or otherwise connected to a distal end of the core wire 30. The core wire 30 may be configured to and/or may be capable of axially translating the left atrial appendage closure device 100 relative to the delivery sheath 40. In one example, the core wire 30 may be advanced distally while the delivery sheath 40 is held in a constant position. In another example, the core wire 30 may be advanced distally while the delivery sheath 40 is retracted proximally. In yet another example, the core wire 30 may be held in a constant position while the delivery sheath 40 is retracted proximally relative to the core wire 30 and/or the left atrial appendage closure device 100. Other configurations are also contemplated. The delivery sheath 40 and/or the core wire 30 may have a selected level of axial stiffness and/or pushability characteristics while also having a selected level of flexibility to permit navigation through the patient's vasculature.

Some suitable, but non-limiting, examples of materials for the left atrial appendage closure device system 10, the core wire 30, the delivery sheath 40, and/or the left atrial appendage closure device 100, etc. are discussed below. It is contemplated that any exemplary left atrial appendage closure device disclosed herein may be used in accordance with and/or be associated with the example left atrial appendage closure device system 10 described above.

The left atrial appendage closure device 100 may comprise an expandable framework 110 configured to shift axially and/or radially along a central longitudinal axis between the fully constrained configuration and the fully unconstrained configuration. In the fully constrained configuration, the expandable framework 110 may be axially elongated and/or radially compressed. In the fully unconstrained configuration, the expandable framework 110 may be axially shortened and/or radially expanded.

Figure 3:
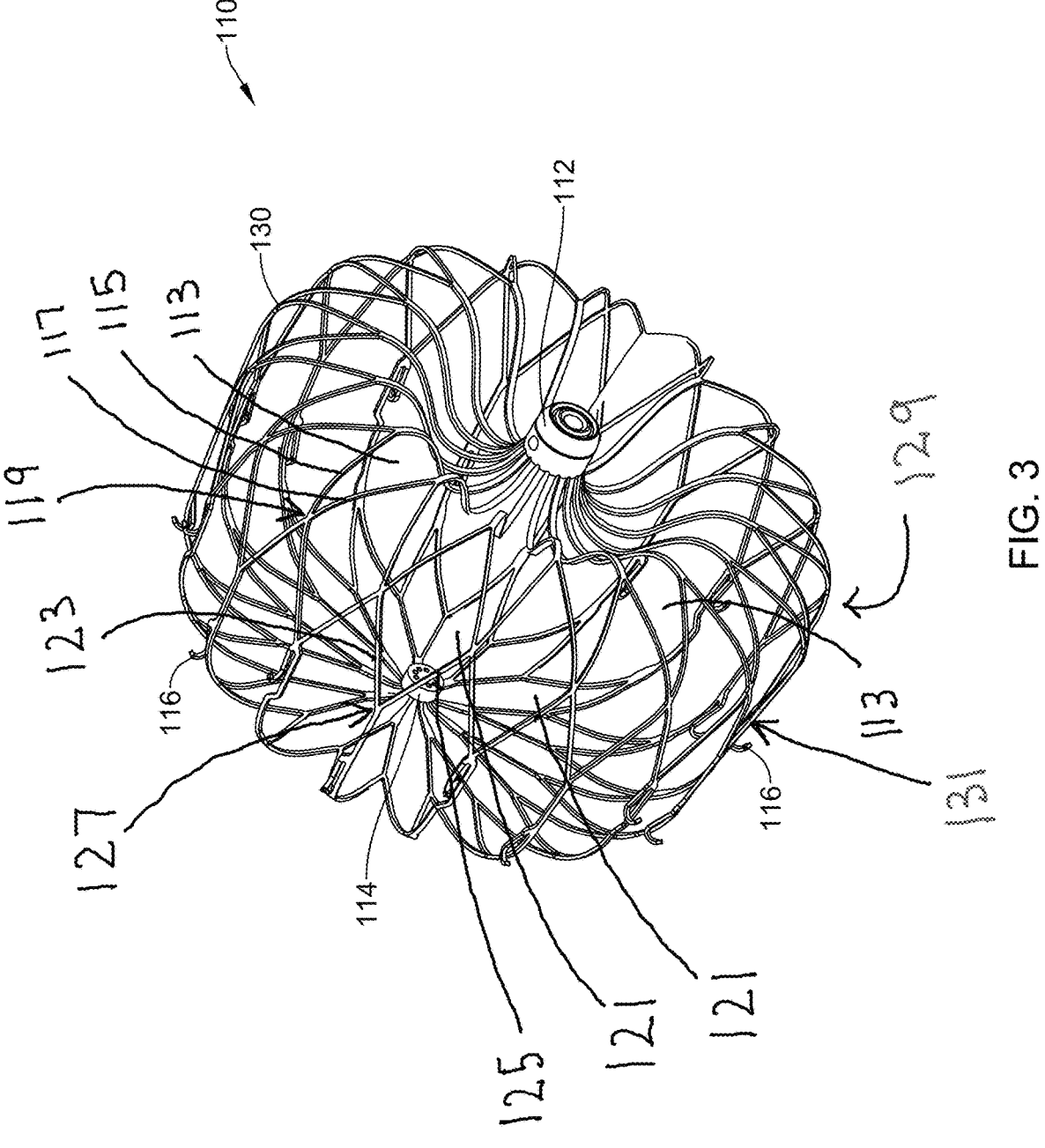
FIG. 3 illustrates selected aspects of a left atrial appendage closure device.

As seen in FIG. 3, which illustrates selected aspects of the left atrial appendage closure device 100 in the fully unconstrained configuration, the expandable framework 110 may have a plurality of struts disposed about the central longitudinal axis. In some embodiments, the plurality of struts may define a plurality of cells. In some embodiments, the plurality of cells may be a plurality of closed cells. In some embodiments, the plurality of cells may be a plurality of open cells. In some embodiments, the plurality of cells may include a plurality of open cells and a plurality of closed cells in various combinations and/or arrangements. FIG. 3 illustrates that the expandable framework 110 may include a first grouping of cells 113, a first row of cells 129, a first strut segment 115, a second strut segment 117, a first node 119, a second grouping of cells 121, a second row 131, a third strut segment 123, a fourth strut segment 125, and a second node 127.

The expandable framework 110 may include a proximal hub 112 and a distal hub 114. In some embodiments, the proximal hub 112 and/or the distal hub 114 may be centered on and/or coaxial with the longitudinal axis. The plurality of struts may be joined together at and/or fixedly attached to the proximal hub 112 and/or the distal hub 114. The proximal hub 112 may be configured to releasably connect, secure, and/or attach the left atrial appendage closure device 100 and/or the expandable framework 110 to the core wire 30. In some embodiments, the proximal hub 112 may include internal threads configured to rotatably and/or threadably engage an externally threaded distal end of the core wire 30. Other configurations for releasably securing the left atrial appendage closure device 100 to the core wire 30 are also contemplated. As noted herein, some features are not shown in every figure to improve clarity.

The expandable framework 110 and/or the plurality of struts may be formed and/or cut from a tubular member. In some embodiments, the expandable framework 110 and/or the plurality of struts may be integrally formed and/or cut from a unitary member. In some embodiments, the expandable framework 110 and/or the plurality of struts may be integrally formed and/or cut from a unitary tubular member and subsequently formed and/or heat set to a desired shape in the fully unconstrained configuration. In some embodiments, the expandable framework 110 and/or the plurality of struts may be integrally formed and/or cut from a unitary flat member or sheet, and then rolled or formed into a tubular structure and subsequently formed and/or heat set to the desired shape in the fully unconstrained configuration. Some exemplary means and/or methods of making and/or forming the expandable framework 110 and/or the plurality of struts include laser cutting, machining, punching, stamping, electro discharge machining (EDM), chemical dissolution, etc. Other means and/or methods are also contemplated.

As would be understood by the skilled person, anatomical features may vary in size and/or shape. In some embodiments, the left atrial appendage may have an irregular (e.g., elongated and/or oblong) cross-sectional shape. In some embodiments, the expandable framework 110 may be compliant and substantially conform to and/or be in sealing engagement with the shape and/or geometry of a lateral wall of a left atrial appendage when deployed and/or expanded therein. In some embodiments, the left atrial appendage closure device 100 may expand to a size, extent, or shape less than or different from the fully unconstrained configuration, as determined by the surrounding tissue and/or lateral wall of the left atrial appendage. In some embodiments, the expandable framework 110 may be configured to shape and/or stretch the tissue of the left atrial appendage such that the lateral wall of the left atrial appendage substantially conforms to an outer shape of the expandable framework 110. Other configurations are also contemplated.

In some embodiments, the expandable framework 110 may include at least one anchoring member 116 extending radially outward therefrom in the fully unconstrained configuration. In some embodiments, the expandable framework 110 may include at least one anchoring member 116 extending radially outward from the expandable framework 110. In some embodiments, the expandable framework 110 may include at least one anchoring member 116 extending radially outward from the expandable framework 110 proximate a proximal shoulder of the expandable framework 110.

In some embodiments, the expandable framework 110 may include at least one anchoring member 116 extending radially outward from the expandable framework 110 proximate a midsection of the expandable framework 110. In some embodiments, the at least one anchoring member 116 may be configured to engage with the lateral wall of the main body of the left atrial appendage. In some embodiments, the at least one anchoring member 116 may be formed as J-shaped hooks having a free end extending in and/or directed toward a proximal direction with respect to the central longitudinal axis of the left atrial appendage closure device 100 and/or the expandable framework 110. Other configurations are also contemplated.

Figure 4:
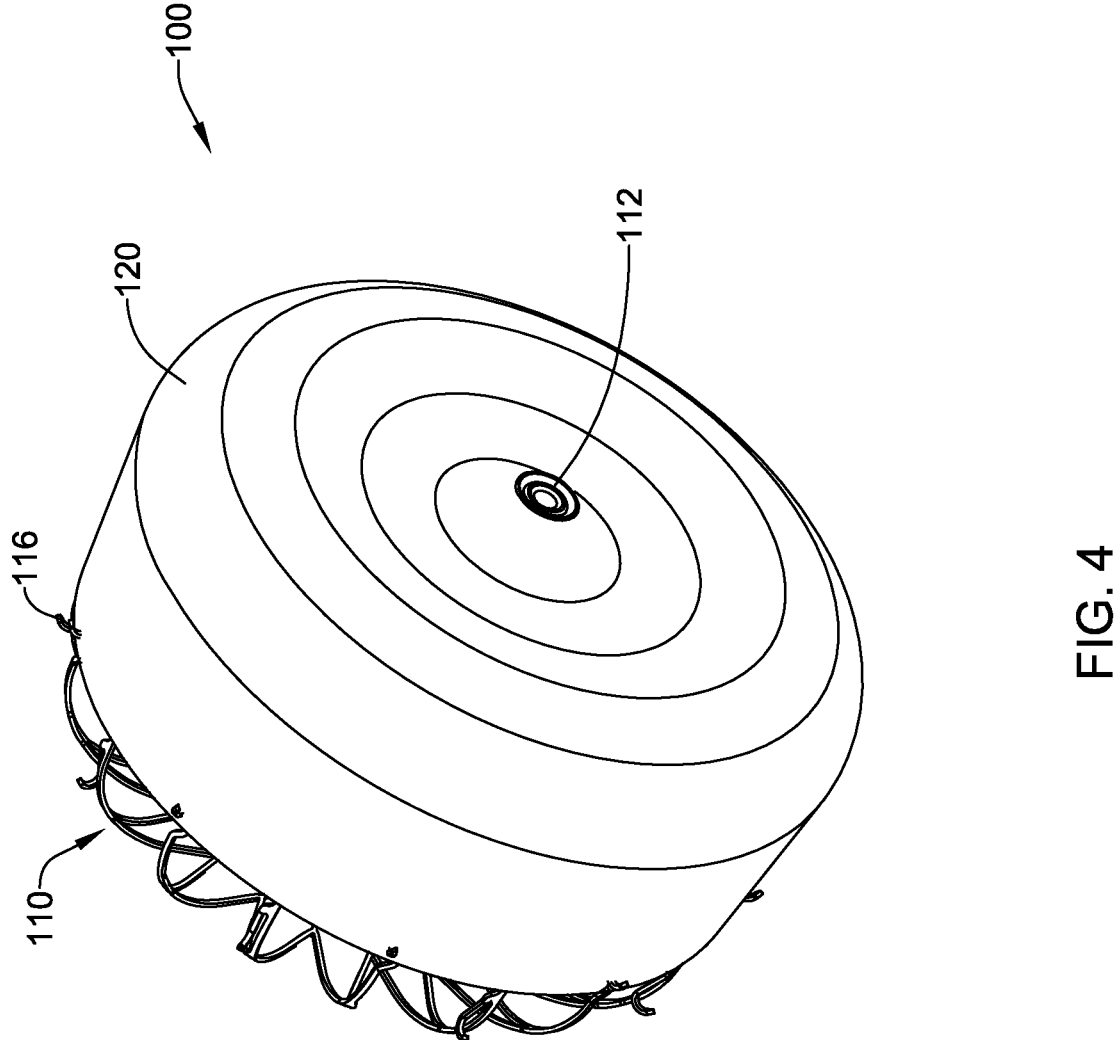
FIG. 4 illustrates selected aspects of the left atrial appendage closure device of FIG. 3.
Figure 5:
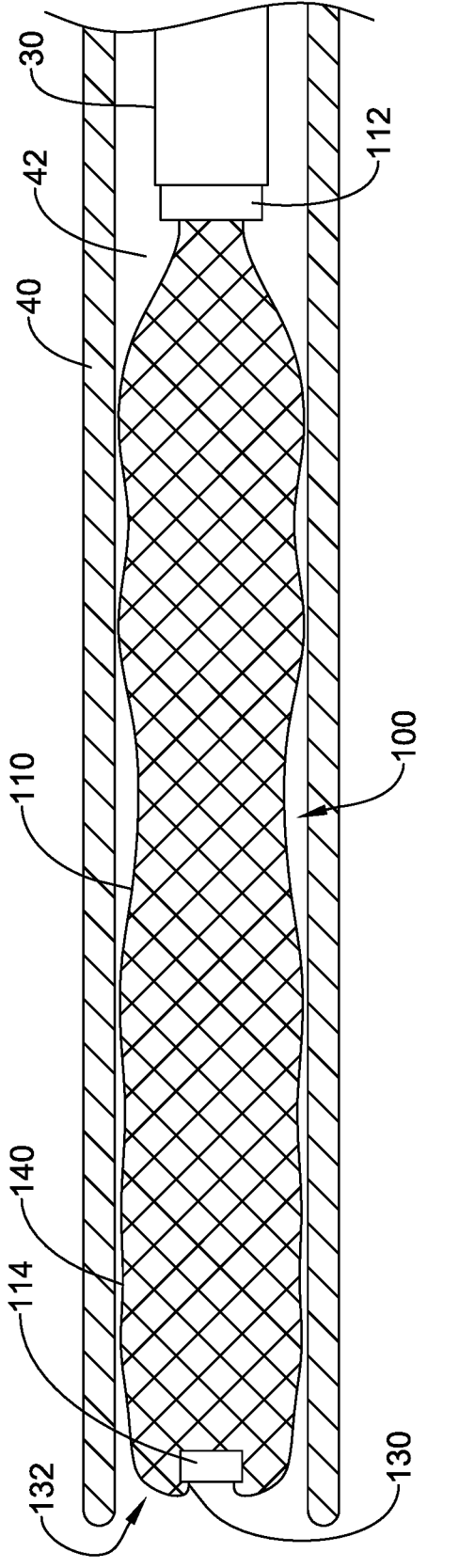
FIGS. 5-9 are schematic partial cross-sectional views illustrating selected aspects related to deploying the left atrial appendage closure device of FIGS. 3-4.

In some embodiments, the left atrial appendage closure device 100 may optionally include the occlusive element 120 connected to, disposed on, disposed over, disposed about, and/or disposed radially outward of at least a portion of the expandable framework 110 and/or the plurality of struts, as seen in FIG. 4. In some embodiments, the occlusive element 120 may be attached to the proximal hub 112 and/or may be attached to the expandable framework at the proximal hub 112. In some embodiments, the occlusive element 120 may extend radially outward from and/or may extend distally from the proximal hub 112. In some embodiments, the occlusive element 120 may be attached and/or secured to the expandable framework 110 at a plurality of discrete locations. In some embodiments, one of, some of, and/or all of the at least one anchoring member 116 may extend through an occlusive element 120, where present.

In some embodiments, the occlusive element 120 may include a membrane, a fabric, a mesh, a tissue element, or another suitable construction. In some embodiments, the occlusive element 120 may be porous. In some embodiments, the occlusive element 120 may be non-porous. In some embodiments, the occlusive element 120 may be permeable to selected gases and/or fluids. In some embodiments, the occlusive element 120 may be substantially impermeable to selected gases and/or fluids, such as blood, water, etc. In some embodiments, the occlusive element 120 may be designed, sized, and/or configured to prevent thrombus and/or embolic material from passing out of the left atrial appendage into the left atrium and/or the patient's bloodstream. In some embodiments, the occlusive element 120 may be configured to promote endothelization after implantation, thereby effectively removing the target site (e.g., the left atrial appendage, etc.) from the patient's circulatory system. Some suitable, but non-limiting, examples of materials for the occlusive element 120 are discussed below.

Figure 7:
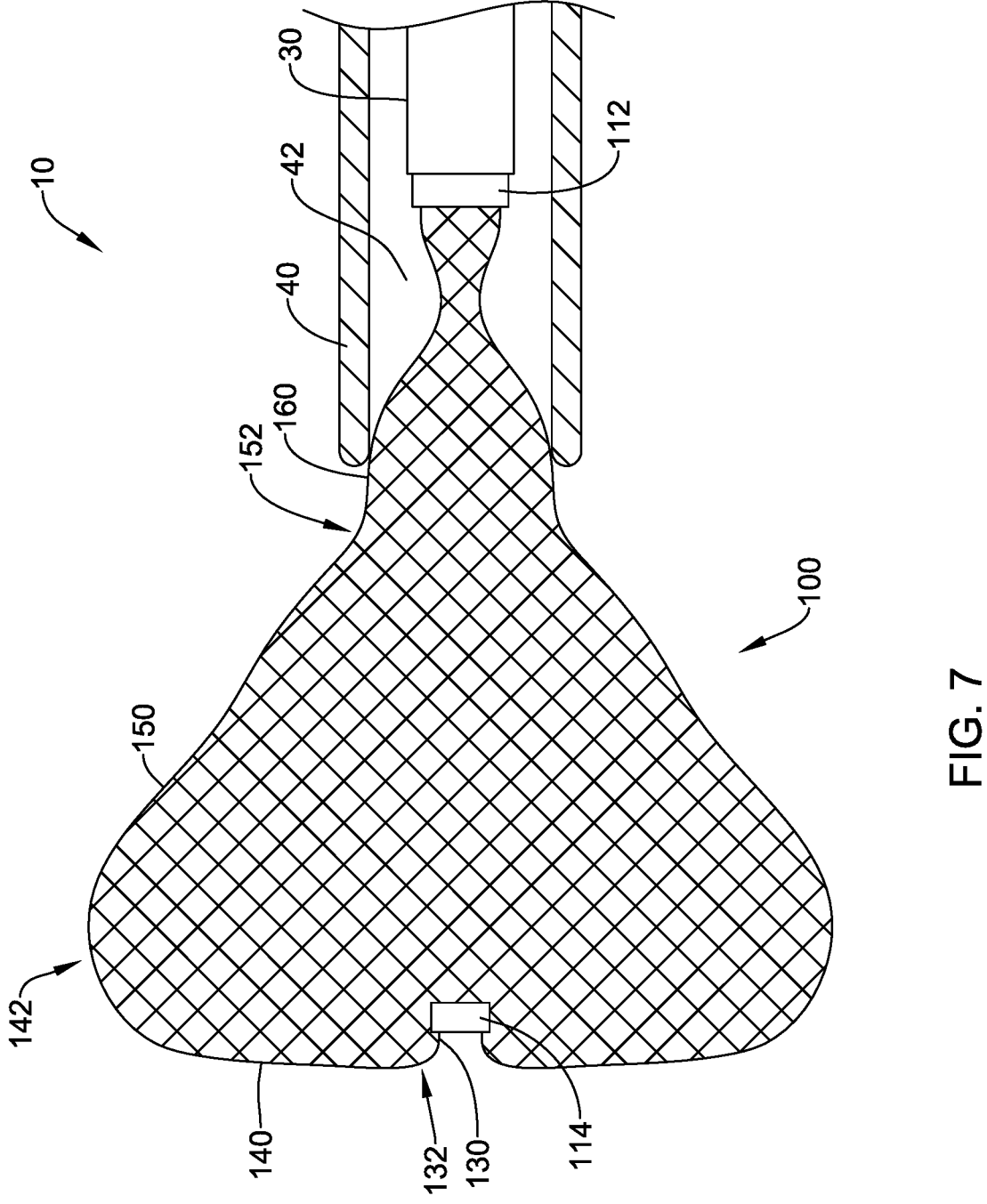
Figure 8:
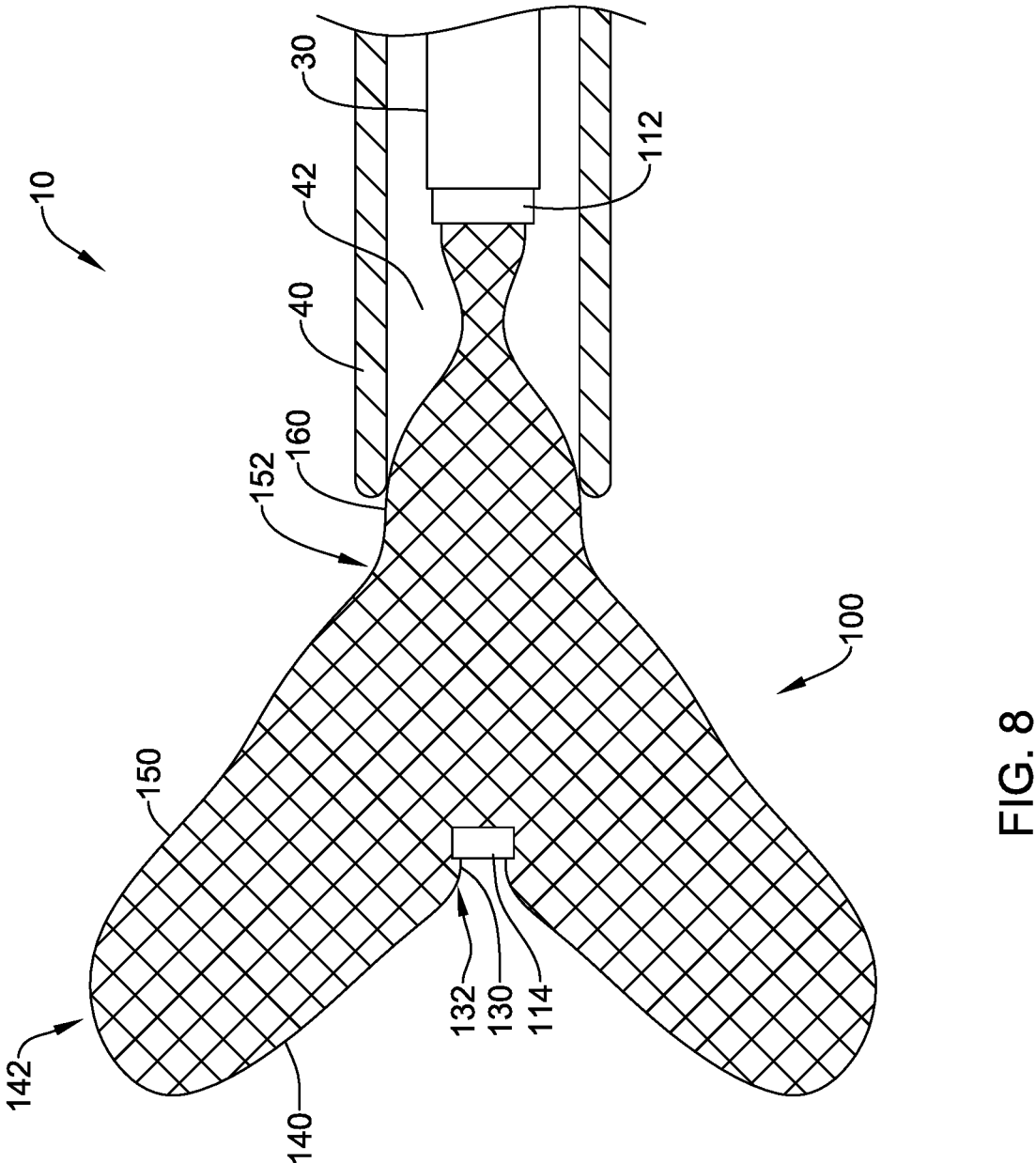
Figure 9:
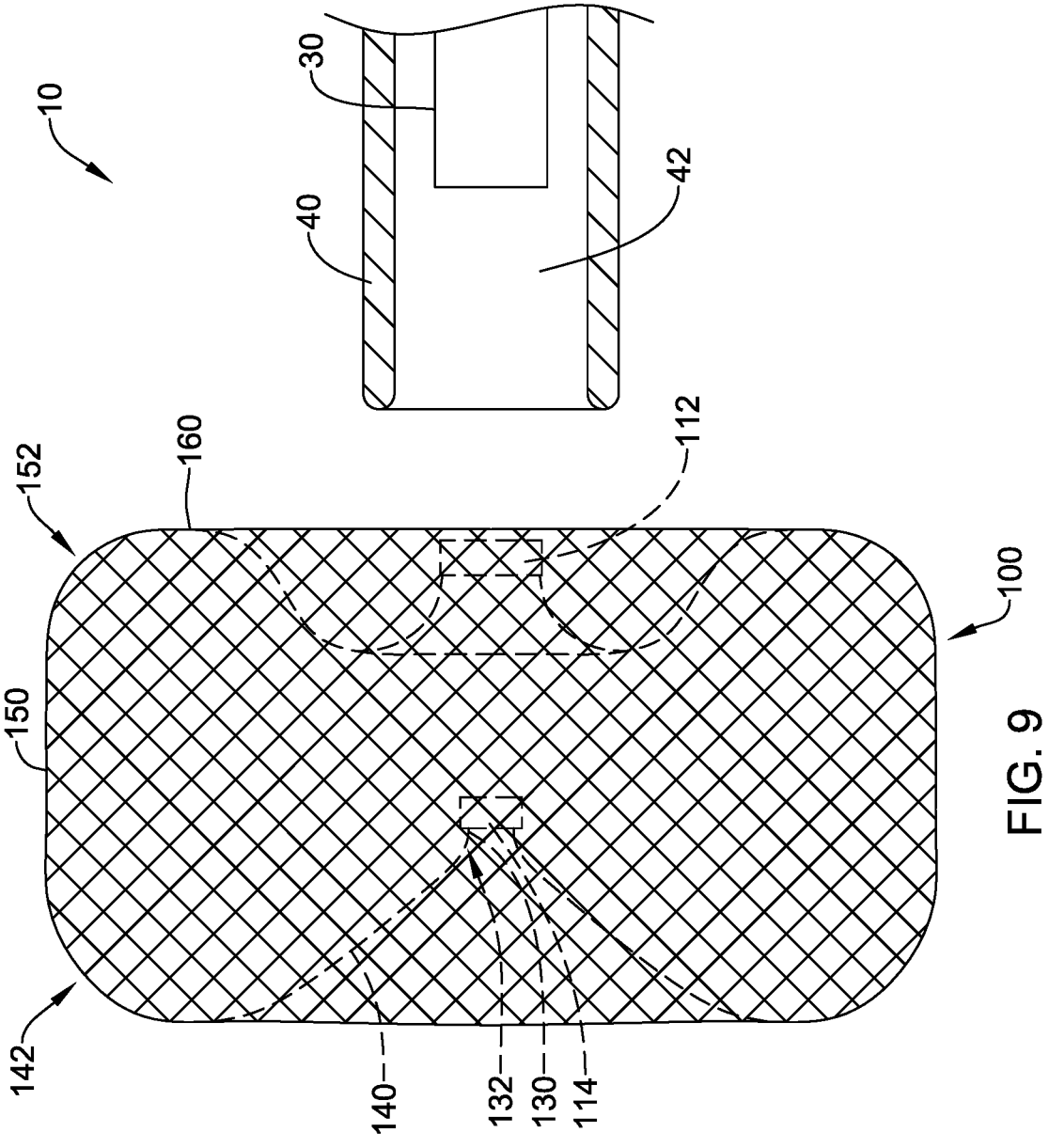

FIGS. 5-9 schematically illustrate selected aspects of the left atrial appendage closure device 100 and/or the left atrial appendage closure device system 10 during deployment of the left atrial appendage closure device 100. For clarity and ease of understanding, some elements of the left atrial appendage closure device 100 are not shown but shall be understood to be present in accordance and/or consistent with other figures and/or description of the disclosure. FIGS. 5-8 illustrate the left atrial appendage closure device 100 in partial cross-section. FIG. 9 illustrates the left atrial appendage closure device 100 using broken lines to show hidden features as may be understood from other figures. The occlusive element 120 is not shown in FIG. 9. It may be seen in FIGS. 5-9 that as the expandable framework 110 of the left atrial appendage closure device 100 shifts from fully constrained to fully unconstrained, the expandable framework 110 may transition sequentially through a plurality of positions. In some embodiments, the plurality of positions may include a first position, a second position, a third position, a fourth position, and/or a fifth position as described herein. In some embodiments, the plurality of positions may include additional and/or other positions.

Returning now to FIG. 5, in some embodiments, the expandable framework 110 may be fully constrained in a first position by the delivery sheath 40. In some embodiments, the expandable framework 110 may be disposed within the lumen 42 of the delivery sheath 40 in the first position. In some embodiments, in the first position a first segment 130 of the plurality of struts of the expandable framework 110 may extend distally from the distal hub 114 substantially parallel to the central longitudinal axis to a first bend 132 and a second segment 140 of the plurality of struts of the expandable framework 110 may extend from the first bend 132 proximally. In some embodiments, in the first position the second segment 140 may extend from the first bend 132 proximally and generally parallel to the central longitudinal axis. In the first position, the distal hub 114 may be disposed proximal of the first bend 132. In some embodiments, the first segment 130 may be secured to the distal hub 114. In some embodiments, the first segment 130 may be fixedly attached to the distal hub 114. For example, the first segment 130 may be welded, adhesively bonded, etc. to the distal hub 114. Other configurations are also contemplated.

Figure 6:
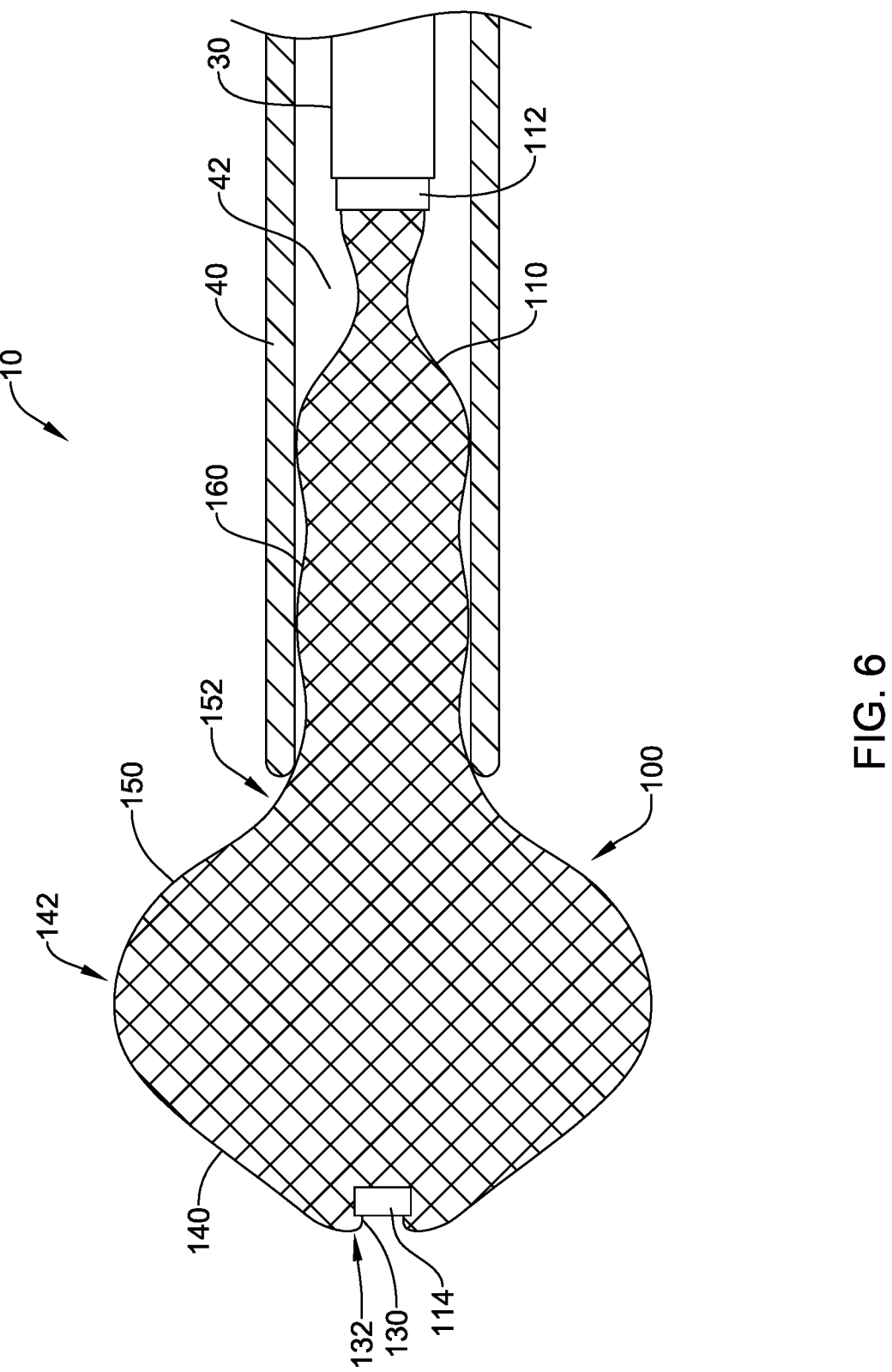

In some embodiments, relative axial translation between the delivery sheath 40 and the expandable framework 110 may expose some of the expandable framework 110 and/or the plurality of struts in a second position, as seen in FIG. 6. In some embodiments, a first amount of the expandable framework 110 and/or the plurality of struts may be exposed from and/or unconstrained by the delivery sheath 40 in the second position. In some embodiments, the first amount may be less than about 55% of an axial length, a volume, a weight, and/or a surface area of the expandable framework 110 and/or the plurality of struts. In some embodiments, the first amount may be about 15% to about 55% of the axial length, the volume, the weight, and/or the surface area of the expandable framework 110 and/or the plurality of struts. Other configurations and/or ranges are also contemplated. In some embodiments, in the second position, the expandable framework 110 may have a maximum radial extent of about 6 millimeters (mm) to about 10 mm. In some embodiments, in the second position, the expandable framework 110 may have a maximum radial extent of about 8 mm. In some embodiments, in the second position, the maximum radial extent of the expandable framework 110 may be about twice or about 200% of a maximum outer extent of a distal end of the delivery sheath 40. Other configurations and/or sizes are also contemplated.

In some embodiments, in the second position the first segment 130 of the plurality of struts of the expandable framework 110 may extend distally from the distal hub 114 substantially parallel to the central longitudinal axis to the first bend 132. In the second position, the second segment 140 of the plurality of struts of the expandable framework 110 may extend from the first bend 132 proximally and radially outward toward and/or to a second bend 142. In the second position, a third segment 150 of the plurality of struts of the expandable framework 110 may extend from the second bend 142 proximally and radially inward toward and/or to a third bend 152. In some embodiments, in the second position, a fourth segment 160 of the plurality of struts of the expandable framework 110 may extend from the third bend 152 proximally to within the lumen 42 of the delivery sheath 40. In some embodiments, in the second position, the fourth segment 160 of the plurality of struts of the expandable framework 110 may extend from the third bend 152 proximally toward the proximal hub 112 disposed within the lumen 42 of the delivery sheath 40.

In some embodiments, in the second position, the distal hub 114 is disposed proximal of the first bend 132. In some embodiments, in the second position, the distal hub 114 may be disposed distal of the second bend 142. For example, in the second position, the distal hub 114 may be positioned distal of a plane extending through, including at least a portion of, and/or tangent to the second bend 142 and oriented perpendicular to the central longitudinal axis. In some embodiments, in the second position, the first segment 130 of the plurality of struts and the second segment 140 of the plurality of struts may form and/or intersect to form an acute angle opening inwardly toward an interior of the expandable framework 110. In some embodiments, in the second position, the first segment 130 of the plurality of struts and the second segment 140 of the plurality of struts may form and/or intersect to form an acute angle opening radially outwardly from the central longitudinal axis. In some embodiments, in the second position, the second segment 140 of the plurality of struts of the expandable framework 110, if swept circumferentially around the central longitudinal axis, may define a generally conical shape tapering radially outward in a proximal direction from the first bend 132 toward the second bend 142.

In some embodiments, relative axial translation between the delivery sheath 40 and the expandable framework 110 may expose more of the expandable framework 110 and/or the plurality of struts in a third position than in the second position, as seen in FIG. 7. In some embodiments, a second amount of the expandable framework 110 and/or the plurality of struts greater than the first amount may be exposed from and/or unconstrained by the delivery sheath 40 in the third position. In some embodiments, the second amount may be less than about 75% of the axial length, the volume, the weight, and/or the surface area of the expandable framework 110 and/or the plurality of struts. In some embodiments, the second amount may be about 40% to about 75% of the axial length, the volume, the weight, and/or the surface area of the expandable framework 110 and/or the plurality of struts. Other configurations and/or ranges are also contemplated.

In some embodiments, in the third position the first segment 130 of the plurality of struts of the expandable framework 110 may extend distally from the distal hub 114 substantially parallel to the central longitudinal axis to the first bend 132. In the third position, the second segment 140 of the plurality of struts of the expandable framework 110 may extend from the first bend 132 radially outward generally perpendicular to the central longitudinal axis toward and/or to the second bend 142. In the third position, the third segment 150 of the plurality of struts of the expandable framework 110 may extend from the second bend 142 proximally and radially inward toward and/or to the third bend 152. In some embodiments, in the third position, the fourth segment 160 of the plurality of struts of the expandable framework 110 may extend from the third bend 152 proximally to within the lumen 42 of the delivery sheath 40. In some embodiments, in the third position, the fourth segment 160 of the plurality of struts of the expandable framework 110 may extend from the third bend 152 proximally toward the proximal hub 112 disposed within the lumen 42 of the delivery sheath 40.

In some embodiments, in the third position, the distal hub 114 is disposed proximal of the first bend 132. In some embodiments, in the third position, the first segment 130 of the plurality of struts and the second segment 140 of the plurality of struts may form and/or intersect to form a generally right angle opening toward the interior of the expandable framework 110. In some embodiments, in the third position, the first segment 130 of the plurality of struts and the second segment 140 of the plurality of struts may form and/or intersect to form a generally right angle opening radially outwardly away from the central longitudinal axis. In some embodiments, in the third position, the second segment 140 of the plurality of struts and the third segment 150 of the plurality of struts may form and/or intersect to form an acute angle opening radially inwardly toward the interior of the expandable framework 110. In some embodiments, in the third position, the second segment 140 of the plurality of struts and the third segment 150 of the plurality of struts may form and/or intersect to form an acute angle opening radially inwardly toward the central longitudinal axis. In some embodiments, in the third position, the third segment 150 of the plurality of struts and the fourth segment 160 of the plurality of struts may form and/or intersect to form an obtuse angle opening radially outwardly away from the central longitudinal axis. In some embodiments, in the third position, the second segment 140 of the plurality of struts of the expandable framework 110, if swept circumferentially around the central longitudinal axis, may define a generally planar shape oriented generally perpendicular to the central longitudinal axis.

In some embodiments, relative axial translation between the delivery sheath 40 and the expandable framework 110 may expose more of the expandable framework 110 and/or the plurality of struts in a fourth position than in the third position, as seen in FIG. 8. In some embodiments, a third amount of the expandable framework 110 and/or the plurality of struts greater than the second amount may be exposed from and/or unconstrained by the delivery sheath 40 in the fourth position. In some embodiments, the third amount may be less than about 95% of the axial length, the volume, the weight, and/or the surface area of the expandable framework 110 and/or the plurality of struts. In some embodiments, the third amount may be about 60% to about 95% of the axial length, the volume, the weight, and/or the surface area of the expandable framework 110 and/or the plurality of struts. Other configurations and/or ranges are also contemplated.

In some embodiments, in the fourth position the first segment 130 of the plurality of struts of the expandable framework 110 may extend distally from the distal hub 114 substantially parallel to the central longitudinal axis to the first bend 132. In the fourth position, the second segment 140 of the plurality of struts of the expandable framework 110 may extend from the first bend 132 distally and radially outward toward and/or to the second bend 142. In the fourth position, the third segment 150 of the plurality of struts of the expandable framework 110 may extend from the second bend 142 proximally and radially inward toward and/or to the third bend 152. In some embodiments, in the fourth position, the fourth segment 160 of the plurality of struts of the expandable framework 110 may extend from the third bend 152 proximally toward the proximal hub 112 disposed within the lumen 42 of the delivery sheath 40.

In some embodiments, in the fourth position, the distal hub 114 is disposed proximal of the first bend 132. In some embodiments, in the fourth position, the first segment 130 of the plurality of struts and the second segment 140 of the plurality of struts may form and/or intersect to form an obtuse angle opening inwardly toward the interior of the expandable framework 110. In some embodiments, in the fourth position, the second segment 140 of the plurality of struts and the third segment 150 of the plurality of struts may form and/or intersect to form an acute angle opening radially inwardly toward the central longitudinal axis. In some embodiments, in the fourth position, the third segment 150 of the plurality of struts and the fourth segment 160 of the plurality of struts may form and/or intersect to form an obtuse angle opening radially outwardly away from the central longitudinal axis. In some embodiments, in the fourth position, the second segment 140 of the plurality of struts of the expandable framework 110, if swept circumferentially around the central longitudinal axis, may define a generally conical shape tapering radially outward in a distal direction from the first bend 132 toward the second bend 142.

In some embodiments, relative axial translation between the delivery sheath 40 and the expandable framework 110 may expose substantially all of the expandable framework 110 and/or the plurality of struts in a fifth position, as seen in FIG. 9. In some embodiments, a fourth amount of the expandable framework 110 and/or the plurality of struts greater than the third amount may be exposed from and/or unconstrained by the delivery sheath 40 in the fifth position. In some embodiments, the fourth amount may be more than about 95% of the axial length, the volume, the weight, and/or the surface area of the expandable framework 110 and/or the plurality of struts. In some embodiments, the fourth amount may be about 100% of the axial length, the volume, the weight, and/or the surface area of the expandable framework 110 and/or the plurality of struts. Other configurations and/or ranges are also contemplated.

In some embodiments, the expandable framework 110 may be in the fully unconstrained configuration in the fifth position. In some embodiments, in the fully unconstrained configuration, the expandable framework may have a maximum radial extent of about 16 millimeters (mm) to about 40 mm. In some embodiments, in the fully unconstrained configuration, the expandable framework may have a maximum radial extent of about 16 mm. In some embodiments, in the fully unconstrained configuration, the expandable framework may have a maximum radial extent of about 20 mm. In some embodiments, in the fully unconstrained configuration, the expandable framework may have a maximum radial extent of about 25 mm. In some embodiments, in the fully unconstrained configuration, the expandable framework may have a maximum radial extent of about 30 mm. In some embodiments, in the fully unconstrained configuration, the expandable framework may have a maximum radial extent of about 35 mm. In some embodiments, in the fully unconstrained configuration, the expandable framework may have a maximum radial extent of about 40 mm. Other configurations and/or sizes are also contemplated.

In some embodiments, in the fifth position the first segment 130 of the plurality of struts of the expandable framework 110 may extend distally from the distal hub 114 substantially parallel to the central longitudinal axis to the first bend 132. In the fifth position, the second segment 140 of the plurality of struts of the expandable framework 110 may extend from the first bend 132 distally and radially outward toward and/or to the second bend 142. In the fifth position, the third segment 150 of the plurality of struts of the expandable framework 110 may extend from the second bend 142 proximally and toward and/or to the third bend 152. In some embodiments, the fifth position, the third segment 150 of the plurality of struts of the expandable framework 110 may extend from the second bend 142 proximally generally parallel to the central longitudinal axis toward and/or to the third bend 152. In some embodiments, in the fifth position, the fourth segment 160 of the plurality of struts of the expandable framework 110 may extend from the third bend 152 radially inward toward and/or to the proximal hub 112.

In some embodiments, in the fifth position, the distal hub 114 is disposed proximal of the first bend 132. In some embodiments, in the fifth position, the first segment 130 of the plurality of struts and the second segment 140 of the plurality of struts may form and/or intersect to form an obtuse angle opening inwardly toward the interior of the expandable framework 110. In some embodiments, in the fifth position, the second segment 140 of the plurality of struts and the third segment 150 of the plurality of struts may form and/or intersect to form an acute angle opening radially inwardly toward the central longitudinal axis. In some embodiments, in the fifth position, the third segment 150 of the plurality of struts and the fourth segment 160 of the plurality of struts may form and/or intersect to form an angle of about 90 degrees or less opening radially inwardly toward the interior of the expandable framework 110. In some embodiments, in the fifth position, the third segment 150 of the plurality of struts and the fourth segment 160 of the plurality of struts may form and/or intersect to form an angle of about 90 degrees or less opening radially inwardly toward the central longitudinal axis.

A method for occluding the left atrial appendage may comprise advancing the left atrial appendage closure device 100 into the left atrial appendage of the patient's heart. For example, the left atrial appendage closure device 100 may be advanced to the left atrial appendage within the lumen 42 of the delivery sheath 40 in the fully constrained configuration. The method may include deploying the expandable framework 110 from the delivery sheath 40 within the left atrial appendage. The method may further include expanding and/or shifting the expandable framework 110 from the fully constrained configuration toward the fully unconstrained configuration within the left atrial appendage.

As the expandable framework 110 shifts from fully constrained to fully unconstrained, the expandable framework 110 may transition sequentially through a plurality of positions, as described herein. In some embodiments, in the second position, the expandable framework 110 may be moved and/or navigated within the patient's heart, the left atrium, and/or the left atrial appendage. In the second position, the expandable framework 110 may form a generally rounded atraumatic shape. In some embodiments, in the second position, the maximum radial extent of the expandable framework 110 may be about twice or about 200% of a maximum outer extent of a distal end of the delivery sheath 40. In some embodiments, in the second position, the maximum radial extent of the expandable framework 110 may be about 8 millimeters. Other configurations and/or sizes are also contemplated. In some embodiments, a physician may use the generally rounded atraumatic shape as a navigational tool within the patient's anatomy.

In and/or near the fully unconstrained configuration (e.g., the fifth position), the expandable framework 110 may be urged into contact with, engaged with, and/or anchored to the lateral wall of the main body of the left atrial appendage. In some embodiments, the expandable framework 110 may not fully achieve the fully unconstrained configuration (e.g., the fifth position) due to contact with the wall(s) of the left atrial appendage. However, the inverted shape of the distal portion of the expandable framework 110 (e.g., the first segment 130, the first bend 132, the second segment 140, and the second bend 142) may prevent the expandable framework 110 from elongating distally, which may compromise locating the left atrial appendage closure device 100 and/or the expandable framework 110 within the left atrial appendage, sealing of the left atrial appendage closure device 100 and/or the expandable framework 110 with respect to the left atrial appendage, and/or anchoring of the left atrial appendage closure device 100 and/or the expandable framework 110 within the left atrial appendage. Instead, compressive force applied against the third segment 150 and/or the second bend 142 may urge the distal hub 114 proximally toward the proximal hub 112. As such, the final shape of the left atrial appendage closure device 100 and/or the expandable framework 110 may be more predictable and locating and anchoring of the left atrial appendage closure device 100 and/or the expandable framework 110 within the left atrial appendage may be improved.

In at least some embodiments, the left atrial appendage closure device 100 and/or the expandable framework 110 may span across the ostium of the left atrial appendage. In some embodiments, the left atrial appendage closure device 100 and/or the expandable framework 110 may span completely across the ostium of the left atrial appendage, thereby effectively removing the left atrial appendage from the circulatory system of the patient.

When satisfied with the positioning of the left atrial appendage closure device 100 within the left atrial appendage, the core wire 30 may be disconnected from the left atrial appendage closure device 100, thereby leaving the left atrial appendage closure device 100 disposed at and/or in the left atrial appendage. In some embodiments, disconnecting the core wire 30 from the left atrial appendage closure device 100 may include rotating the externally threaded distal end of the core wire 30 relative to the left atrial appendage closure device 100 and/or the proximal hub 112 to disengage the core wire 30 from the left atrial appendage closure device 100.

In some embodiments, the delivery sheath 40 and/or the core wire 30 may include a keying structure configured to prevent rotation of the core wire 30 relative to the proximal hub 112. In such embodiments, the keying structure is disengaged prior to rotating the core wire 30 relative to the left atrial appendage closure device 100 and/or the proximal hub 112. When the keying structure is engaged, rotation of the core wire 30 may be transmitted to left atrial appendage closure device 100 and/or the expandable framework 110. In some embodiments, rotation of the left atrial appendage closure device 100 and/or the expandable framework 110 may facilitate positioning and/or orientation of the left atrial appendage closure device 100 and/or the expandable framework 110 relative to the left atrial appendage, for example, with respect to an asymmetrical and/or irregular ostium and/or left atrial appendage. Other configurations, purposes, and/or results are also contemplated.

The materials that can be used for the various components of the system (and/or other elements disclosed herein) and the various components thereof disclosed herein may include those commonly associated with medical devices and/or systems. For simplicity purposes, the following discussion refers to the system. However, this is not intended to limit the devices and methods described herein, as the discussion may be applied to other elements, members, components, or devices disclosed herein, such as, but not limited to, the left atrial appendage closure device, the delivery sheath, the core wire, the expandable framework, the occlusive element, etc. and/or elements or components thereof.

In some embodiments, the system and/or components thereof may be made from a metal, metal alloy, polymer (some examples of which are disclosed below), a metal-polymer composite, ceramics, combinations thereof, and the like, or other suitable material.

Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTEL-LOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybde-num alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super-elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a some-what, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super-elastic nitinol in that linear elastic and/or non-super-elastic nitinol may accept up to about 2-5% strain while remaining substantially elastic (e.g., before plastically deforming) whereas super-elastic nitinol may accept up to about 8% strain before plastically deforming. Both of these materials can be dis-tinguished from other linear elastic materials such as stain-less steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large tem-perature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be gen-erally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or prop-erties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Mate-rial Co. of Kanagawa, Japan. Other suitable materials may include ULTANIUM™ (available from Neo-Metrics) and GUM METAL™ (available from Toyota). In some other embodiments, a superelastic alloy, for example a superelas-tic nitinol can be used to achieve desired properties.

In at least some embodiments, portions or all of the system and/or other elements disclosed herein may also be doped with, made of, or otherwise include a radiopaque material. Radiopaque materials are understood to be mate-rials capable of producing a relatively bright image on a fluoroscopy screen or another imaging technique during a medical procedure. This relatively bright image aids a user in determining the location of the system and/or other elements disclosed herein. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the system and/or other elements disclosed herein to achieve the same result.

In some embodiments, a degree of Magnetic Resonance Imaging (MRI) compatibility is imparted into the system and/or other elements disclosed herein. For example, the system and/or components or portions thereof may be made of a material that does not substantially distort the image and create substantial artifacts (e.g., gaps in the image). Certain ferromagnetic materials, for example, may not be suitable because they may create artifacts in an MRI image. The system or portions thereof, may also be made from a material that the MM machine can image. Some materials that exhibit these characteristics include, for example, tung-sten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the system and/or other elements disclosed herein may be made from or include a polymer or other suitable material. Some examples of suitable polymers may include polytetrafluoroethylene (PTFE), ethylene tet-rafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), poly-vinylchloride (PVC), polyether-ester (for example, ARNI- TEL® available from DSM Engineering Plastics), ether or ester based copolymers (for example, butylene/poly(al-kylene ether) phthalate and/or other polyester elastomers such as HYTREL® available from DuPont), polyamide (for example, DURETHAN® available from Bayer or CRISTA-MID® available from Elf Atochem), elastomeric poly-amides, block polyamide/ethers, polyether block amide (PEBA, for example available under the trade name PEBAX®), ethylene vinyl acetate copolymers (EVA), sili-cones, polyethylene (PE), MARLEX® high-density poly-ethylene, MARLEX® low-density polyethylene, linear low density polyethylene (for example REXELL®), polyester, polybutylene terephthalate (PBT), polyethylene terephtha-late (PET), polytrimethylene terephthalate, polyethylene naphthalate (PEN), polyetheretherketone (PEEK), polyim-ide (PI), polyetherimide (PEI), polyphenylene sulfide (PPS), polyphenylene oxide (PPO), poly praraphenylene terephtha-lamide (for example, KEVLAR®), polysulfone, nylon, nylon-12 (such as GRILAMID® available from EMS American Grilon), perfluoro(propyl vinyl ether) (PFA), eth-ylene vinyl alcohol, polyolefin, polystyrene, epoxy, polyvi-nylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the system and/or other elements disclosed herein may include a fabric material disposed over or within the structure. The fabric material may be com-posed of a biocompatible material, such a polymeric mate-rial or biomaterial, adapted to promote tissue ingrowth. In some embodiments, the fabric material may include a bio-absorbable material. Some examples of suitable fabric mate-rials include, but are not limited to, polyethylene glycol (PEG), nylon, polytetrafluoroethylene (PTFE, ePTFE), a polyolefinic material such as a polyethylene, a polypropyl-ene, polyester, polyurethane, and/or blends or combinations thereof.

In some embodiments, the system and/or other elements disclosed herein may include and/or be formed from a textile material. Some examples of suitable textile materials may include synthetic yarns that may be flat, shaped, twisted, textured, pre-shrunk or un-shrunk. Synthetic biocompatible yarns suitable for use in the present disclosure include, but are not limited to, polyesters, including polyethylene tere-phthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytet-rafluoroethylenes, and the like. The yarns may be of the multifilament, monofilament, or spun types. The type and denier of the yarn chosen may be selected in a manner which forms a biocompatible and implantable prosthesis and, more particularly, a vascular structure having desirable properties.

In some embodiments, the system and/or other elements disclosed herein may include and/or be treated with a suitable therapeutic agent. Some examples of suitable thera-peutic agents may include anti-thrombogenic agents (such as heparin, heparin derivatives, urokinase, and PPack (dextro-phenylalanine proline arginine chloromethylketone)); anti-proliferative agents (such as enoxaparin, angiopeptin, mono-clonal antibodies capable of blocking smooth muscle cell proliferation, hirudin, and acetylsalicylic acid); anti-inflam-matory agents (such as dexamethasone, prednisolone, cor-ticosterone, budesonide, estrogen, sulfasalazine, and mesalamine); antineoplastic/antiproliferative/anti-mitotic agents (such as paclitaxel, 5-fluorouracil, cisplatin, vinblas-tine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin com-pounds, platelet receptor antagonists, anti-thrombin antibod-ies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcrip-tional activators, and translational promoters); vascular cell growth inhibitors (such as growth factor inhibitors, growth factor receptor antagonists, transcriptional repressors, trans-lational repressors, replication inhibitors, inhibitory antibod-ies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vaso-active mechanisms.

It should be understood that this disclosure is, in many respects, only illustrative. Changes may be made in details, particularly in matters of shape, size, and arrangement of steps, without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A medical implant, comprising:

an expandable framework having a plurality of struts disposed about a central longitudinal axis, the plurality of struts being joined at a proximal hub and a distal hub;

wherein the plurality of struts of the expandable frame-work are formed from a unitary tubular member:

wherein the expandable framework includes a proximal shoulder region extending from the proximal hub to a proximal shoulder region end point, and wherein the expandable framework includes a distal shoulder region extending from the distal hub to a distal shoulder region end point; and wherein the portion of the expandable framework extend-ing between the proximal shoulder region end point and the distal shoulder region end point is substantially parallel to the central longitudinal axis; and wherein the plurality of struts extending between the proximal hub and the distal hub define an interior volume of the expandable framework, and wherein the proximal hub is located outside the interior volume of the expandable framework and the distal hub is located within the interior volume of the expandable frame-work;

wherein in a fully unconstrained configuration of the expandable framework, a first segment of the plurality of struts extends distally from the distal hub to a first bend, and a second segment of the plurality of struts extends from the first bend distally and radially outward to a second bend.

2. The medical implant of claim 1, wherein the proximal shoulder region includes a first grouping of cells adjacent to the proximal hub and defining a first row, and wherein a first cell in the first row of cells includes a first strut segment and a second strut segment joined at a first distal node.

3. The medical implant of claim 2, wherein the first row of cells extends circumferentially around the central longitudinal axis of the expandable framework.

4. The medical implant of claim 3, wherein the expandable framework further includes a second grouping of cells defining a second row adjacent to the first row, and wherein a second cell in the second row of cells includes a third strut segment and a fourth strut segment joined at a second distal node.

5. The medical device of claim 4, wherein the width of at least one cell of the second grouping of cells is different than the width of the cells defining the first grouping of cells.

6. The medical device of claim 5, wherein the width of at least one cell of the second grouping of cells is wider than the width of the cells defining the first grouping of cells.

7. The medical implant of claim 1, further comprising a membrane disposed along an outer surface of the expandable framework.

8. The medical implant of claim 7, wherein the membrane extends along the outer surface of the expandable framework from the proximal hub to a membrane end point, and wherein the membrane end point is positioned along the portion of the expandable framework that is substantially parallel to the central longitudinal axis.

9. The medical implant of claim 8, wherein the membrane end point is positioned at a second node of the second grouping of cells.

10. The medical implant of claim 1, wherein the expandable framework further includes a plurality of fixation members disposed thereon.

11. The medical implant of claim 10, wherein the plurality of fixation members are formed from the unitary tubular member.

12. The medical implant of claim 11, wherein at least a portion of the plurality of fixation members extend through an aperture formed in the membrane.

13. The medical implant of claim 1, wherein the plurality of struts extending between the proximal hub and the distal hub define an interior volume of the expandable framework, and wherein the proximal hub is located outside the interior volume of the expandable framework and the distal hub is located within the interior volume of the expandable framework, and wherein when in the expanded configuration, the distal hub is positioned proximal of a distalmost extent of the expandable framework.

14. The medical implant of claim 1, wherein the expandable framework is configured to shift between a first unexpanded configuration and an expanded configuration, and wherein when in the expanded configuration, the distal hub is positioned proximal of a distalmost extent of the expandable framework.

15. An occlusive implant, comprising:
an expandable framework having a plurality of struts disposed about a central longitudinal axis, the plurality of struts being joined at a proximal hub and a distal hub;
wherein the plurality of struts of the expandable framework are formed from a unitary tubular member;

wherein the expandable framework includes a proximal shoulder region extending from the proximal hub to a proximal shoulder region end point; and wherein the expandable framework includes a distal shoulder region extending from the distal hub to a distal shoulder region end point; and wherein the portion of the expandable framework extending between the proximal shoulder region end point and the distal shoulder region end point is substantially parallel to the central longitudinal axis; and wherein the plurality of struts extending between the proximal hub and the distal hub define an interior volume of the expandable framework, and wherein the proximal hub is located outside the interior volume of the expandable framework and the distal hub is located within the interior volume of the expandable framework;

wherein when the expandable framework is disposed within a delivery sheath in a fully constrained configuration, a first segment of the plurality of struts extends distally from the distal hub to a first bend, and a second segment of the plurality of struts extends from the first bend proximally;

wherein in a fully unconstrained configuration of the expandable framework, the first segment of the plurality of struts extends distally from the distal hub to the first bend, and the second segment of the plurality of struts extends from the first bend distally and radially outward to a second bend;

a membrane disposed along an outer surface of the expandable framework, wherein the membrane extends along the outer surface of the expandable framework from the proximal hub to a membrane end point; and a plurality of fixation members disposed along the expandable framework.

16. The occlusive implant of claim 15, wherein the membrane end point is positioned along the portion of the expandable framework that is substantially parallel to the central longitudinal axis.

17. The occlusive implant of claim 16, wherein the expandable framework and the plurality of fixation members are formed from a unitary tubular member.

18. The occlusive implant of claim 17, wherein at least a portion of the plurality of fixation members extend through an aperture formed in the membrane.

19. The occlusive implant of claim 15, wherein the plurality of struts extending between the proximal hub and the distal hub define an interior volume of the expandable framework, and wherein the proximal hub is located outside the interior volume of the expandable framework and the distal hub is located within the interior volume of the expandable framework.

20. A method for occluding a left atrial appendage of a patient, the method comprising:
positioning an occlusive implant adjacent the left atrial appendage, the occlusive implant including:
an expandable framework having a plurality of struts disposed about a central longitudinal axis, the plurality of struts being joined at a proximal hub and a distal hub;
wherein the plurality of struts of the expandable framework are formed from a unitary tubular member;
wherein the expandable framework includes a proximal shoulder region extending from the proximal hub to a proximal shoulder region end point; and
wherein the expandable framework includes a distal shoulder region extending from the distal hub to a distal shoulder region end point, and wherein the portion of the expandable framework extending between the proximal shoulder region end point and the distal shoulder region end point is substantially parallel to the central longitudinal axis; and wherein the plurality of struts extending between the proximal hub and the distal hub define an interior volume of the expandable framework, and wherein the proximal hub is located outside the interior volume of the expandable framework and the distal hub is located within the interior volume of the expandable framework;

wherein in a fully unconstrained configuration of the expandable framework, a first segment of the plurality of struts extends distally from the distal hub to a first bend, and a second segment of the plurality of struts extends from the first bend distally and radially outward to a second bend;

a membrane disposed along an outer surface of the expandable framework, wherein the membrane extends along the outer surface of the expandable framework from the proximal hub to a membrane end point; and a plurality of fixation members disposed along the expandable framework; and expanding the occlusive implant within the left atrial appendage such that the membrane extends across an ostium of the left atrial appendage.

* * * * *